(12) United States Patent
Hale

(10) Patent No.: US 12,208,285 B2
(45) Date of Patent: *Jan. 28, 2025

(54) BORE BASED MEDICAL SYSTEM COMPRISING A CAMERA CARRIER CONFIGURED TO BE MOUNTED IN THE BORE-BASED MEDICAL SYSTEMS AND UTILIZED FOR POSITIONING AND MONITORING OF PATIENTS DURING RADIOTHERAPY TREATMENT

(71) Applicant: Vision RT Limited, London (GB)

(72) Inventor: Gideon M. Hale, London (GB)

(73) Assignee: VISION RT LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/505,441

(22) Filed: Nov. 9, 2023

(65) Prior Publication Data

US 2024/0075317 A1 Mar. 7, 2024

Related U.S. Application Data

(63) Continuation of application No. 18/101,840, filed on Jan. 26, 2023, now Pat. No. 11,850,447, which is a (Continued)

(30) Foreign Application Priority Data

Nov. 12, 2019 (EP) ..................................... 19208457
Jan. 10, 2020 (EP) ..................................... 20151106

(51) Int. Cl.
*A61N 5/10* (2006.01)

(52) U.S. Cl.
CPC ......... *A61N 5/1049* (2013.01); *A61N 5/1001* (2013.01); *A61N 5/103* (2013.01); (Continued)

(58) Field of Classification Search
CPC .... A61N 5/1049; A61N 5/1001; A61N 5/103; A61N 5/1075; A61N 5/1081; (Continued)

(56) References Cited

U.S. PATENT DOCUMENTS 10,035,026 B2 7/2018 Tijs et al.
11,590,365 B2* 2/2023 Hale .................... A61N 5/1081
(Continued)

FOREIGN PATENT DOCUMENTS

JP 2019-188137 A 10/2019

OTHER PUBLICATIONS

Japanese Office Action for Japanese Application No. 2020-187307, dated May 21, 2024, with English translation.

*Primary Examiner* — Courtney D Thomas
(74) *Attorney, Agent, or Firm* — Birch, Stewart, Kolasch & Birch, LLP

(57) ABSTRACT

Disclosed is a bore based medical system comprising a camera carrier configured to be mounted in the bore based medical system and configured to monitor and/or track patient motion within said bore based medical system during radiotherapy, the bore based medical system comprising a rotatable ring-gantry configured to emit a radiotherapy beam focused at an iso-center of the bore based medical system, wherein the ring-gantry is configured to rotate at least partly around a through-going bore having a front side and a back side, configured to receive from said front side, a movable couch configured to be moved into and out from the through-going bore, wherein further the through-going bore comprises an inner side facing an inside of the bore, and wherein the camera carrier is configured to be mounted inside the bore in connection with the inner side of the through-going bore.

19 Claims, 14 Drawing Sheets

Related U.S. Application Data continuation of application No. 17/087,710, filed on Nov. 3, 2020, now Pat. No. 11,590,365.

(52) U.S. Cl.
CPC ......... *A61N 5/1075* (2013.01); *A61N 5/1081* (2013.01); *A61N 2005/1019* (2013.01); *A61N 2005/1059* (2013.01); *A61N 2005/1072* (2013.01)

(58) Field of Classification Search
CPC .... A61N 2005/1019; A61N 2005/1059; A61N 2005/1072; A61N 2005/1056; A61N 2005/1076; A61B 5/1113; A61B 6/035; A61B 5/0077; A61B 5/1128; A61B 6/04; A61B 6/4435; A61B 5/0035
See application file for complete search history.

(56) References Cited

U.S. PATENT DOCUMENTS

| | | |
|---|---|---|
| 11,850,447 B2 * | 12/2023 | Hale ..................... A61B 5/1113 |
| 2010/0059679 A1 | 3/2010 | Albrecht |
| 2016/0249984 A1 | 9/2016 | Janssen |
| 2017/0143271 A1 | 5/2017 | Gustafsson et al. |
| 2017/0319143 A1 | 11/2017 | Yu et al. |
| 2018/0192984 A1 | 7/2018 | Lee et al. |
| 2019/0321657 A1 | 10/2019 | Hale |

* cited by examiner

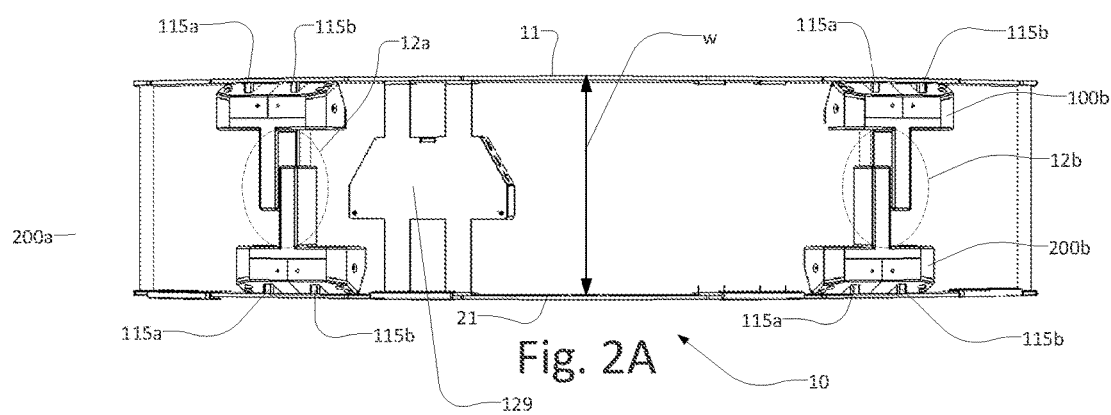
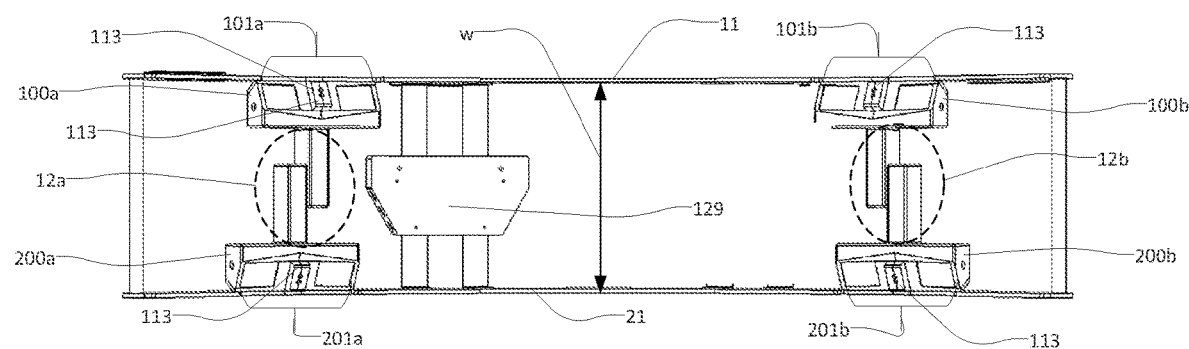

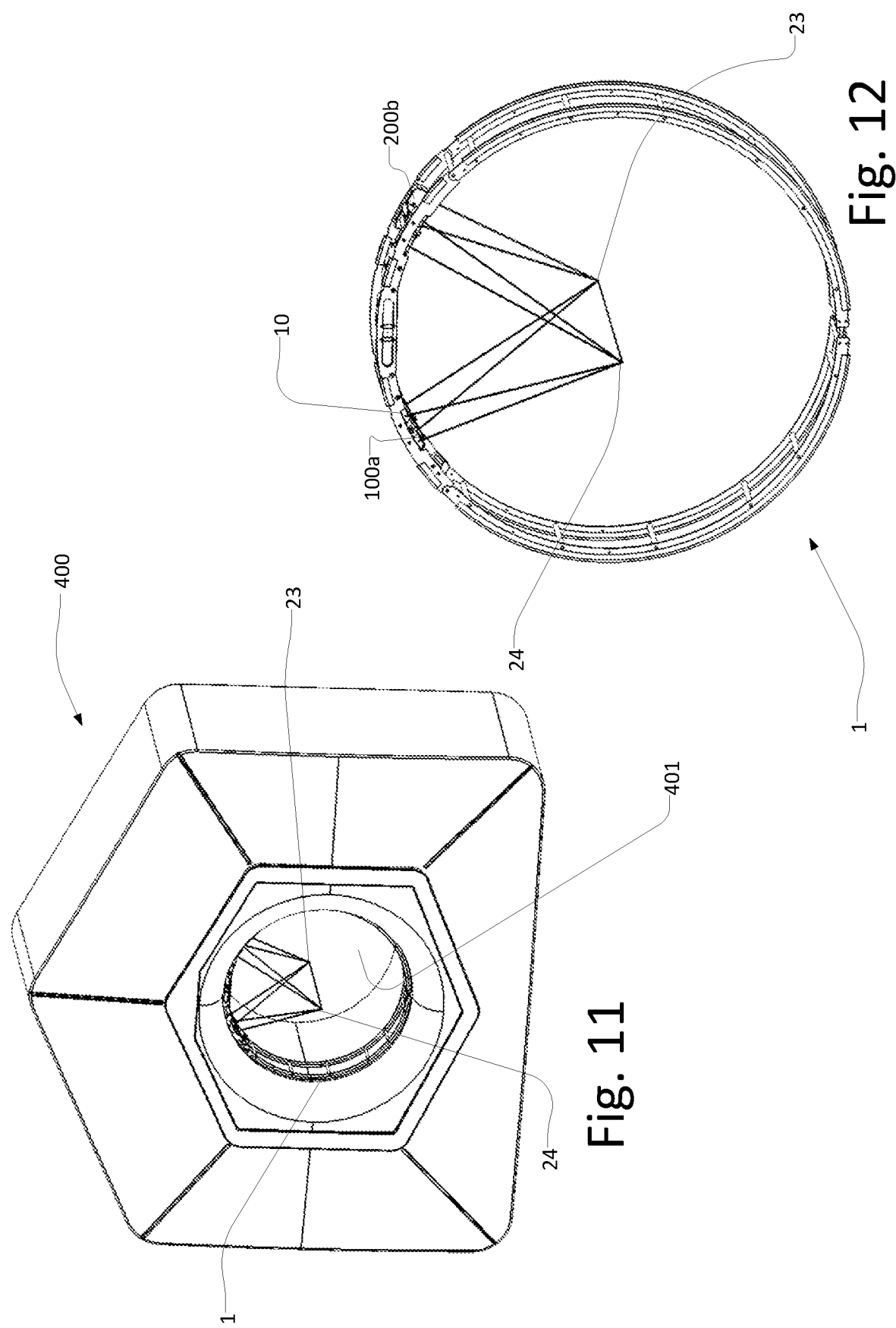

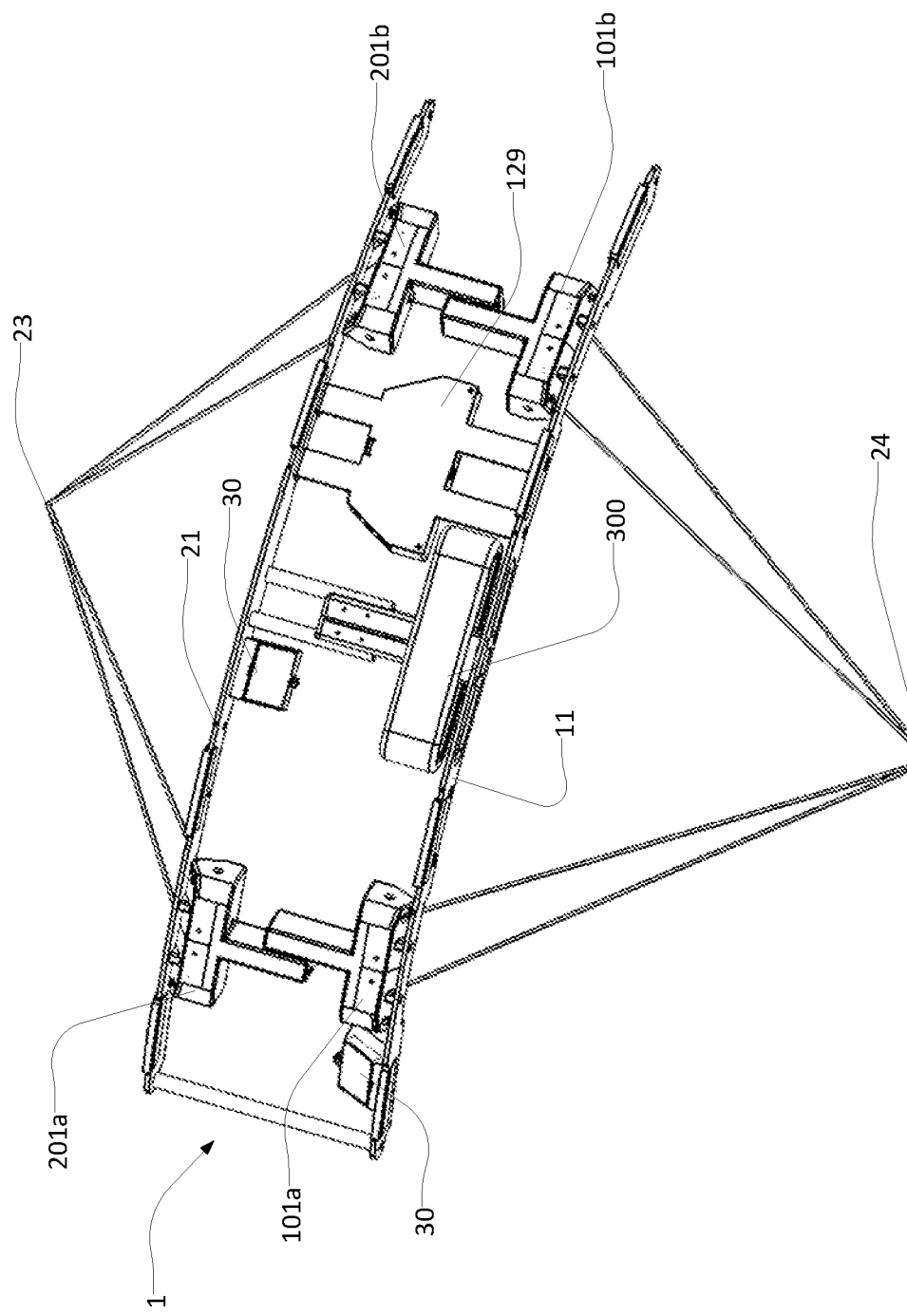

BORE BASED MEDICAL SYSTEM COMPRISING A CAMERA CARRIER CONFIGURED TO BE MOUNTED IN THE BORE-BASED MEDICAL SYSTEMS AND UTILIZED FOR POSITIONING AND MONITORING OF PATIENTS DURING RADIOTHERAPY TREATMENT

CROSS-REFERENCE TO RELATED APPLICATIONS

This application is a Continuation of application Ser. No. 18/101,840, filed Jan. 26, 2023, which is a Continuation of application Ser. No. 17/087,710, filed on Nov. 3, 2020 (now U.S. Pat. No. 11,590,365, issued on Feb. 28, 2023), which claims priority under 35 U.S.C. § 119(a) to Application No. 19208457.2 filed in Europe on Nov. 12, 2019 and Application No. 20151106.0 filed in Europe on Jan. 10, 2020, all of which are hereby expressly incorporated by reference into the present application.

BACKGROUND

The present disclosure relates to a bore based medical system having a camera carrier mounted therein. The camera carrier is configured to be mounted in the bore based medical system, such as a bore-based imaging and/or treatment system. More particularly, the disclosure relates to a camera carrier construction mounted in the bore based medical system and having one or more cameras arranged integral to the through-going bore of the bore based medical system to allow monitoring and tracking of patient motion during radiotherapy treatment. The one or more cameras is configured to monitor a patient lying on a couch of the system during a setup stage of medical diagnostic imaging or treatment of the patient; monitor any movement of the patient on the couch in a treatment stage; and/or to also monitor any movement of the couch during medical imaging or treatment of the patient. To monitor the patient, especially in the treatment stage, it is important that accurate imaging of the patient can be performed, why it is important that a sufficient view of the patient via e.g. camera technology can be obtained.

In medical diagnostic imaging and treatment applications used in e.g. cancer diagnostics and treatment, there is a need to be able to monitor the patient during for example cancer treatment to ensure that the correct target tissue of the patient is treated sufficiently without causing damage to healthy tissue. Further to be able to align the treatment setup with the correct target area it is important to ensure that a patient during e.g. scanning methodologies, such as CT and MR imaging, is positioned in a manner which can be transferred into the treatment room. Accordingly, in conventional cancer diagnosis and treatment, the patient is for diagnostic and planning purposes positioned in a CT and/or MR scanner to evaluate the target tissue to be treated. Preceding the planning stage, the patient is moved to e.g. a radiotherapy room, wherein a linear accelerator, such as a Linac radiotherapy machine (also known as a gantry) is utilized to treat the cancer tissue of the patient with radiation therapy. Especially during treatment, it is important that any potential movement of the patient is monitored and registered in order to be able to halt the treatment to avoid any unintentional damage to healthy tissue areas of the patient. Thus, in conventional radiotherapy treatment rooms, a set of monitoring cameras are often utilized to monitor patient movement during treatment. Furthermore, such cameras are also configured to be utilized as positioning setup cameras, whereby the health care professionals in a radiotherapy treatment room is aided in ensuring that the patient is correctly positioned on a couch of the treatment—especially in view of positioning the patient correctly in relation to a treatment isocenter and the target tissue to be exposed to radiotherapy. Such conventional radiotherapy rooms are normally configured with a C-arm radiotherapy system, and thus monitoring cameras have a sufficient field of view for monitoring of the patient and the treatment room since the cameras are often mounted in e.g. ceiling areas of the treatment room.

However, unlike these conventional linear accelerators, recently developed bore-based medical systems, such as radiotherapy bore-based medical systems restrict the view of ceiling mounted cameras, why the monitoring of patients and thus any displacement of the target tissue in relation to the radiotherapy beam, especially during treatment may be limited in such systems.

Thus, to be able to sufficiently monitor and track any potential movement of a patient in a bore-based medical system, during e.g. radiotherapy treatment, there is a need to re-think existing camera solutions. Therefore, there is a need to provide a solution that addresses at least some of the above-mentioned problems, where the present disclosure provides at least new alternative solutions for positioning and monitoring of a patient within a bore-based medical system.

SUMMARY

An aspect of the disclosure is to provide a bore based medical system (e.g., a CT or MR scanner, or linac radiotherapy machine) comprising a camera carrier configured to be mounted in the bore based medical system and configured to monitor and/or track patient motion within said bore based medical system during radiotherapy. The bore based medical system comprises a gantry taking the form of a rotatable ring (hereinafter referred to as a "rotatable ring-gantry," or "ring-gantry" for short). The configured to emit a radiotherapy beam focused at an iso-center of the bore based medical system, the iso-center being the point in space around which components of the ring-gantry rotates, wherein the ring-gantry is configured to rotate at least partly around a through-going bore having a front side and a back side. The through-going bore is configured to receive from the front side, a movable couch configured to be moved into and out from the through-going bore, wherein further the ring-gantry is housed by a gantry housing, which includes a cylindrical (or substantially cylindrical) wall defining a circumference of the through-going bore (such wall being hereinafter referred to as a "bore wall"), the bore wall having a surface facing the inside of the through-going bore (such surface hereinafter being referred to as an "inner surface" of the in-bore wall), and wherein the camera carrier is configured to be mounted inside the bore in connection with the inner surface of the bore wall. Furthermore, the bore based medical system comprises the camera carrier integrated therein, wherein the camera carrier comprises at least two treatment monitoring cameras mounted in connection with the inner surface of the bore wall and together configured to cover a field of view including the focus point of the radiotherapy beam, which is at the iso-center, and thus is hereinafter referred to as the "iso-center focus point" of the bore based medical system. The two treatment monitoring cameras are configured to record images of the patient lying on said movable couch during radiotherapy treatment so as to allow monitoring and/or tracking of any motion performed by said patient. This solution gives provision for a camera system mounted in a bore-based medical system which is optimized especially motion tracking of a patient lying on a couch within the bore-based medical system. A bore based system according to the invention allows for maintaining a good viewing angle of the patient inside the bore via the two monitoring cameras during treatment of the patient. Furthermore, by integrating the two treatment monitoring cameras with the bore wall of the system, the camera carrier provides a stable mounting of the cameras inside the bore. The stable mounting of the two treatment monitoring camera within the internal structure of the bore based medical system is important in view of maintaining inter-camera calibration as well as absolute position of the cameras forming part of the camera carrier.

In general, it should be noted that through-out the disclosure, the camera carrier is described to form a carrier body where at least the two treatment monitoring cameras can be mounted. However, as will be apparent, the two treatment monitoring cameras may also be configured to be mounted directly on internal structures of the inner surface of the bore wall. That is, in one embodiment, the gantry housing of the bore based medical system may comprise an internal space between the bore wall and another outer facing side of the gantry housing, wherein the rotatable gantry is configured to rotate within the internal space and the two treatment monitoring cameras are configured to be mounted within the internal space. The bore wall may in such embodiment be configured with a transparent area, at a wavelength visible to cameras, for each of the treatment monitoring cameras allowing the treatment monitoring cameras to record the images of the patient positioned within the field of view of the treatment monitoring cameras at least covering the iso-center focus point of the bore based medical system.

It should be noted that in one embodiment, the transparent area may also merely be a hole in the material of the bore wall through which the cameras may be able to "look" out from. Thus, the lenses of the cameras (i.e. the camera viewing surface) does not need to be covered by a further layer of material when mounted integral to the inner side of the bore. Rather the "viewing surface" of the cameras may be substantially flush with the inner side.

As previously mentioned, the two treatment monitoring cameras may be mounted on a carrier body, wherein the treatment monitoring cameras are mounted on the carrier body at an equal distance from a symmetric line of the carrier body. In this way it is ensured that the treatment monitoring cameras when mounted in the through-going bore cover the substantially same field of view having at least the iso-center focus point of the bore based medical system contained therein.

Generally, the two treatment monitoring cameras could be consider to be any camera suitable for providing 3D camera technologies, where such 3D cameras technology that can be used with the current setup includes structured Light cameras, Time of Flight, Laser Scanning cameras and/or any other suitable 3D surface tracking camera.

The carrier body may comprise a camera viewing surface facing an iso-center focus point of the bore based medical system, and the two treatment monitoring cameras may be configured so that internal camera mirrors of two treatment monitoring cameras is angled in relation to the camera viewing surface. In this way it is ensured that the cameras when inserted into a bore may cover a field of view containing the iso-center focus point and at least a part of the patient.

In general, when inserting cameras into a generally bore-based medical system, it is important that the cameras are angled with the correct angle to cover a sufficient part of the patient, including the iso-center focus point, which contains e.g. a tumor target tissue to be treated. Due to the substantially "rounded" inner surface of the bore wall of a bore based medical system it can be difficult to mount the treatment monitoring cameras, so that they 1) do not take up too much space within the bore and 2) contains a sufficient field of view of be able to track any patient motion during radiotherapy treatment. With the solutions provided herein, as described, the camera carrier and the mounting of the cameras within the bore provides an efficient solution, allowing a good field of view coverage by the cameras within the bore without taking too much space within the bore. The more detailed construction and positioning of the cameras within the through-going bore allowing a sufficient field of view will become apparent throughout the disclosure, with special reference to the detailed description of the figures.

It should be noted that in one embodiment, the camera carrier of the bore based medical system may furthermore comprise a set of two setup cameras having a front viewing surface facing substantially in an opposite direction to said two treatment monitoring cameras and facing a front viewing area of the bore based medical system, wherein said two setup cameras are configured with a field of view covering at least a part of the couch when said couch is positioned outside of said through-going bore.

Both the setup cameras (also denoted front part cameras throughout the disclosure) and the treatment monitoring cameras (also denoted back part cameras throughout the disclosure) described herein is preferably used for generating a 3D surface of a patient when the patient is positioned in a couch of a bore-based medical system. The 3D surface generated from images recorded by the cameras are used to track any potential motion of the patient during a treatment and or setup stage of e.g. a radiotherapy treatment session. That is, in the setup-stage of a system according to the disclosure, the front part cameras (i.e. setup cameras) described are utilized to record images of a patient positioned on a couch outside of the bore of the bore-based medical system. In this setup-stage the front part cameras records images of the patient so as to allow a surface generation of the patient, which assist the health clinicians using the system to position the patient correctly on the couch in view of e.g. treating a target area containing e.g. cancer.

In the preceding treatment-stage, the couch with the patient is moved into the inside of the through-going bore of the bore-based medical system, wherein the back part cameras (i.e. the treatment monitoring cameras) is configured to monitor continuously any motion of the patient during treatment, via the creation of a surface of the patient and a subsequent tracking of any movement of the generated surface from an initial given position. In this way the back part cameras can monitor the patient directly within the bore, which solves the existing problems with not having a sufficient view of the patient, when using cameras positioned outside of the bore. For these reasons, the front part cameras will also in the following be referred to as setup cameras and the back part cameras referred to as treatment monitoring cameras. Further the back part cameras, may prior to the actual treatment be configured to confirm that patient has not moved while being transported into the bore. Thus, one could say that a positioning check can be performed by the back part cameras, before starting the treatment and thus allowing the cameras to monitor continuously any movement of the patient during treatment.

As is already apparent, the treatment monitoring cameras and the setup cameras may be mounted on the same camera carrier within the bore and/or on separate camera carriers, where at least the treatment monitoring cameras will always be positioned within the bore—either internal to the structures (e.g., walls) defining the circumference of the bore or externally placed on the inner surface of the bore wall.

In an embodiment, the camera carrier may be configured with a substantially ring-shaped body (i.e. a carrier body), wherein the two setup cameras are configured to be mounted in relation to said bore based system substantially back to back with each of the two treatment monitoring cameras so as to form a first back-to-back and a second back-to-back camera configuration. In other words the camera carrier may comprise a first substantially back-to-back camera configuration, wherein a first front part camera is mounted substantially back-to-back with a first back part camera of the camera carrier, and a second back-to-back camera configuration, wherein a second front part camera is mounted substantially back-to-back with a second back part camera of the camera carrier, wherein each of the front part cameras and back part cameras is configured so that internal camera mirrors of said front part and back part cameras is angled in relation to the front viewing surface and the back viewing surface, respectively. By providing an angled mirror construction in each of the cameras it is ensured that a camera surface of the cameras can be aligned in parallel with a surface of the camera carrier ring-body while at the same time ensuring a viewing angle covering the patient lying substantially below the cameras. Furthermore, the back-to-back configurations of the 4 cameras (2 cameras for each back-to-back configuration) ensures a compact, rigid and stable camera carrier which is easily mounted in the bore-based medical system.

In a further embodiment of the camera carrier one or more of each of the front part and back part cameras may comprise a projector configured to project a light onto a target configured to be arranged within a field of view of one or more cameras. The projected light may assist in the 3D surface generation provided by the camera carrier. That is, when the light is projected onto an object within the field of view of the cameras, this light, preferably a structured or patterned light, may be recorded by the cameras, which ease the subsequent image processing and 3D object (or patient) surface generation of the images generated by the cameras. It should be noted that the 3D surface generation may take place in imaging software provided with the cameras or alternatively in an image software provided external to the cameras.

In an embodiment, the camera carrier may be configured such that each of the one or more cameras (i.e. one or more of the two setup cameras and/or one or more of the two treatment monitoring cameras) each comprises at least two internal mirrors, wherein a first mirror is arranged at a first end surface of the camera and a second mirror at a second end surface of the camera, wherein each of the mirrors comprises a mirror center and wherein a mirror center axis is defined between said mirror centers, the mirrors being configured to reflect incoming light onto an image sensor of the camera.

In an embodiment, the first and second mirror for all of the mentioned cameras herein, is arranged so as to form a mirror angle between a mirror plane and the viewing surface of the camera, wherein the mirror angle is configured to be 45 degrees or above.

In an embodiment, the one or more cameras described herein, specially the setup and treatment monitoring cameras may comprise at least a first image sensor configured to be arranged on a substrate of the camera at a distance from a first mirror center, and a second image sensor configured to be arranged at an opposite side of the substrate at a distance from a second mirror center, wherein said mirror plane of each of the first mirror and second mirror are configured with said mirror angle $\alpha_1$ equal $\alpha_2$, and wherein the first and second sensor comprises a first sensor axis and a second sensor axis perpendicular to the first sensor axis, wherein at least one of said first sensor axis or second sensor axis is arranged normal the plane of the viewing surface and parallel with a first minor axis of said mirror plane.

It should be noted that the mirror configuration and sensor configuration ensures together that the cameras are provided with the correct field of view of a setup focus point (for the front part cameras) and a iso-center focus point (for the back part cameras), when the cameras are mounted in the bore-based medical system. It allows, as previously mentioned, the top surface of the cameras to be mounted substantially parallel with a top surface of the ring-shaped body. In other words, the camera body should not be angled in relation to the ring-shaped body to allow the mirrors and sensors of the cameras to provide a field of view of the cameras covering the setup-focus point and the iso-center focus point.

In a further embodiment, the camera carrier may further comprise a third front camera configured as a couch monitoring camera. This third front camera may be mounted in relation to the bore based medical system so as to be substantially mid-centered in relation to the first back-to-back and second back-to-back camera configuration, wherein the couch monitoring camera is configured with a lens orientation having a field of view covering at least a part of a couch of said bore-based medical system in a mounted state of said couch monitoring camera. This provides a possibility of the camera carrier being able to track any couch movement and provide an error estimate of e.g. an iso-center deviation or e.g. a couch sag or deviation in view of pre-calibrated parameters.

In an embodiment, the ring-shaped body may comprise a focus point, wherein said first back-to-back camera configuration and said second back-to-back camera configuration is arranged in or on said ring-shaped body at a substantial identical radial distance and field of view angle from said focus point. It should be noted that the focus-point mentioned here is in relation to the front part cameras. That is, the focus point mentioned should be construed as e.g. the setup focus point. The focus-point of the front part cameras are different from that of the back-part cameras, since the front and back part cameras are pointing in opposite directions. However, all 4 cameras, each of the 2 front part cameras and each of the 2 back part cameras are arranged on the camera carrier at an equal distance from said focus point ensuring that the front part cameras covers a field of view of the same focus point (i.e. setup focus point) and ensuring that the back part cameras convers a field of view of the same focus point (i.e. iso-center focus point).

Accordingly, in an embodiment, the front part and second front cameras comprises a field of view intersecting at a setup focus point of said camera carrier, and wherein said back camera and second back camera comprises a field of view intersecting a treatment focus point of bore-based medical system.

In an embodiment the at least one or more cameras are mounted in a first arch of the ring-shaped body. The first arch may comprise a front body part and a back body part, wherein the front and back body part is connected so as to form a width of the partly ring-shaped body; wherein the treatment monitoring cameras are configured to be mounted at said partly ring-shaped body at an equal distance from a symmetric line of said partly ring-shaped body. It should be noted that this mentioned first arch comprising one or more of the mentioned cameras may be mounted within an internal space of the gantry housing between the bore wall and an opposing wall of the gantry housing. However, as will be apparent through-out the disclosure, the arch could also be mounted externally on the inner surface of the bore wall. This construction allows for an easy installation and removal of the camera carrier in a bore based medical system during e.g. service of the system and or calibration or re-positioning of the system.

In a further development of this embodiment, the first arch in a first end is configured to be connected to a left arch and in a second end is configured to be connected to a right arch, wherein each of the left and right arches is connected via a substantially flexible joint to the first arch. This construction allows for an easy installation and removal of the camera carrier in a bore based medical system.

In a further embodiment the left and right arches may be connected through an adjustable expansion element, wherein the expansion element may be configured to be adjusted to a first expansion stage forcing said left and right arch away from each other and a second stage relieving the first expansion stage. By this construction, the left and right arches may be expanded to allow the arches to abut and connect with an inside of a bore-based medical system in a frictional manner. The expansion element could be considered as an adjustable spring solution, which ensures that the camera carrier can rigidly be mounted in the bore-based medical system. Thus, and an easy installation and removal of the camera carrier in the bore of the bore-based medical system is provided.

In yet a further embodiment, the camera carrier may comprise on at least at parts of the camera carrier, a gasket mounted on an outer periphery of said camera carrier.

The function of the camera carrier is to be mounted in a bore-based medical system of e.g. a radiotherapy system, wherein the camera carrier is configured to monitor patient during a setup stage and/or during a treatment stage. Thus, in an aspect of the disclosure, a bore-based medical system is provided for. The bore-based medical system is configured to receive therein the camera carrier described in embodiments herein, wherein the bore-based medical system comprises: a ring-gantry on which is mounted a radiotherapy beam source configured to emit a radiotherapy beam, wherein said ring-gantry is disposed in a gantry housing so as to surround a through-going bore configured to receive a movable couch configured to be moved into and out from the bore, wherein the gantry housing comprises an in-bore wall (i.e., a cylindrical, or substantially cylindrical, wall defining a circumference of a through going bore) with an inner surface (i.e., surface facing an inside of the bore), and wherein the camera carrier is configured to be mounted inside the bore in an inner space defined (partly) by the bore wall.

In an embodiment, the bore-based medical system is configured with an iso-center and a setup focus point, wherein the setup focus point is configured as point of correct positioning of a patient in view of a target area of the patient to be treated, and the iso-center is configured as a focus point at which an axis of rotation of the gantry, a collimator of the bore-based medical system and the treatment couch intersects, wherein the camera carrier is configured to be mounted in said bore-based medical system so as to ensure that at least one of the one or more cameras is configured and oriented to comprise a field of view covering the iso-center in a mounted stage of the camera carrier, and at least a second of the one or more cameras is configured and oriented to comprise a field of view covering the setup focus point in a mounted stage of the camera carrier.

In a further embodiment, the bore-based medical system is configured to receive within the bore of the system the camera carrier, wherein the camera carrier is arranged within said through going bore at a mid-point between said setup focus point and said iso-center.

Through-out the disclosure a bore-based imaging and/or treatment system will be mentioned. It should be understood that such system can be comprised by e.g. a CT scanner, MR scanners, and/or Bore-based radiotherapy systems. In general, the camera carrier described herein is considered to be suitable for use in such systems, when the medical imaging and/or treatment systems is constructed as a bore, wherein the patient is positioned on a couch within the bore during medical imaging and/or treatment. The bore-based system is configured as a structure enclosing a through-going bore, wherein in the through going bore a couch can be moved in and out therefrom. Within the enclosing structure of the bore a CT medical imaging system, a MR system, or a radiotherapy linac accelerator can be integrated. Thus, a bore wall that defines the circumference of the bore, which together with an outer-facing surface defines a hollow inner structure of the gantry housing, wherein components of e.g. a CT scanner, MR scanner and/or Radiotherapy linac accelerator equipment is installed. More specially, in a bore based medical imaging and/or radiotherapy system, the apparatus may comprise a ring gantry which is configured to apply a beam of radiation towards a target area of a patient during cancer treatment.

BRIEF DESCRIPTION OF DRAWINGS

The aspects and embodiments of the disclosure may be best understood from the following detailed description taken in conjunction with the accompanying Figures. The Figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 2A illustrates a top view of the camera carrier in FIG. 1A;

FIG. 2B illustrates a bottom view of the camera carrier in FIG. 1A;

FIG. 11 is a schematic illustration of a bore-based medical system having the camera carrier mounted therein and where the setup focus point and the iso-center focus point of the camera carrier is illustrated;

FIG. 12 is an illustration of a camera carrier mounted in the bore-based medical system of FIG. 11, wherein the setup focus point and the iso-center focus point of the camera carrier is illustrated;

FIG. 13 illustrates an embodiment of the camera carrier according to FIGS. 2A and 2B, wherein the setup focus point and the iso-center focus point of the camera carrier is illustrated together with a camera hub, a couch monitoring camera and further LED's of the camera carrier.

DETAILED DESCRIPTION

The detailed description set forth below in connection with the appended drawings is intended as a description of various configurations. The detailed description includes specific details for the purpose of providing a thorough understanding of various embodiments of the disclosure. However, it will be apparent to those skilled in the art that these embodiments may be practiced without these specific details. Several aspects of the apparatus and the corresponding system (including methods thereof) using the apparatus will be described, and all of the aspects should be considered to be part of the combined disclosure and function of the apparatus and system. Thus, in the following description of embodiments of the apparatus and system each of the features and methods of the apparatus and system will be described independently and should be implemented in the described working relationship.

Bore Based Medical System

Figure 10:
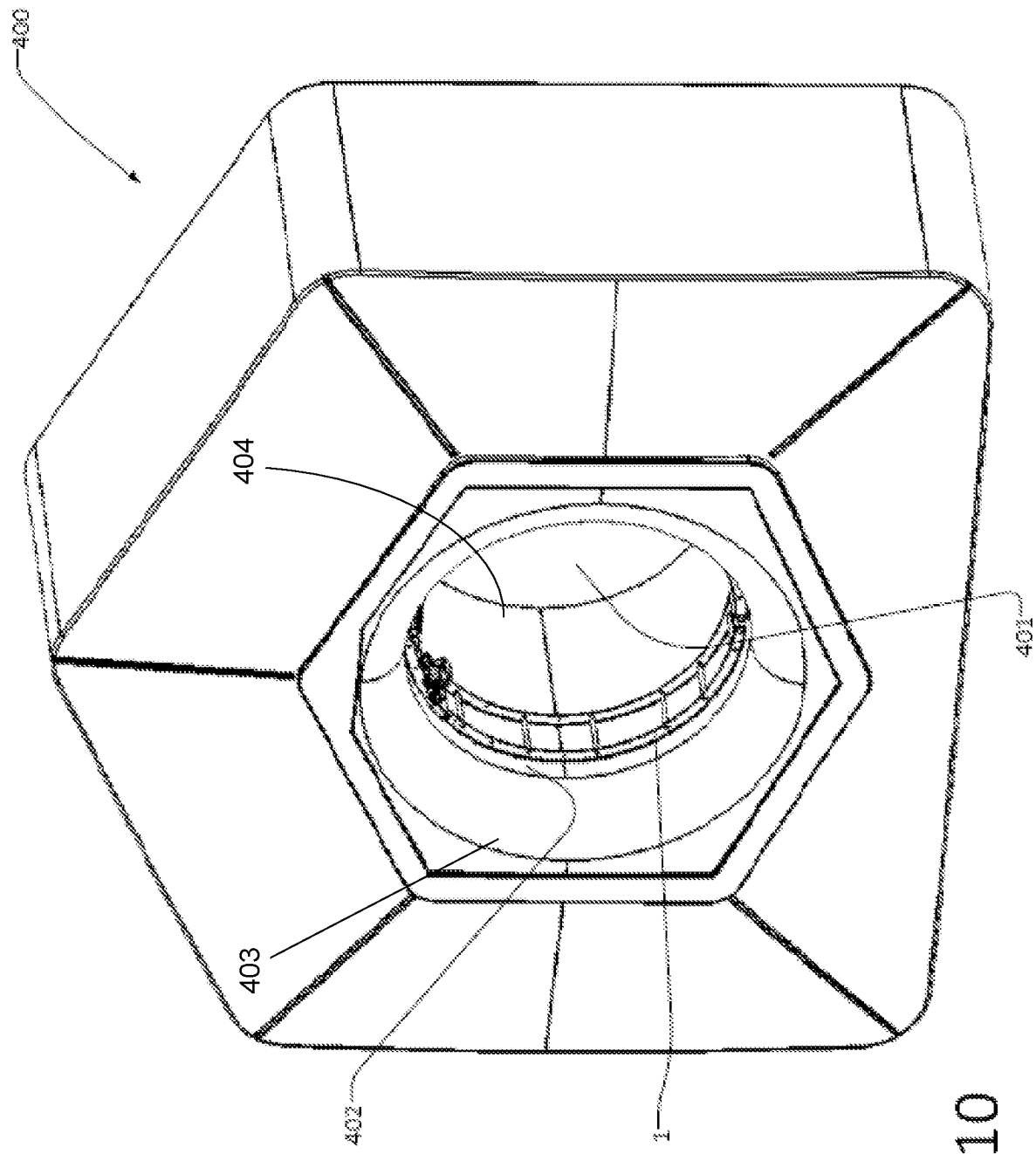
FIG. 10 illustrates the camera carrier in an embodiment when mounted in a bore-based medical system.

Starting from FIG. 10, a bore based medical system 400 (e.g., CT or MR scanner, or linac radiotherapy machine) comprising a camera carrier 1 configured to be mounted in the bore based medical system 400 and configured to monitor and/or track patient motion within said bore based medical system during radiotherapy is illustrated. As illustrated, the bore based medical system 400 is configured with an outer frame structure 407 having a front side 403 and a back side 404. Further, as shown, e.g., in FIGS. 10 and 15, the frame structure 407 includes a cylindrical (or substantially) cylindrical wall, hereinafter referred to as a "bore wall," configured to define the circumference of a through-going bore 401. The surface of the bore wall, facing the through-going bore 401, will be referred to as an "inner surface" 402 of the bore wall. The bore based medical system 400 comprises a gantry taking the form of a rotatable ring (hereinafter referred to as a "rotatable ring-gantry," or "ring-gantry" for short). This ring-gantry has mounted thereon a radiotherapy beam source (not shown). The point in space within the through-going bore 407, around which the components of the ring-gantry rotate, is the iso-center. The radiotherapy beam source is configured to emit a radiotherapy beam focused at the iso-center, and thus the focus point of the radiotherapy beam source will hereinafter be referred to as an "iso-center focus point" of the bore based medical system. The ring-gantry is configured to rotate within the frame structure 407, so as to be invisible for the naked eye when looking at the bore based medical system. Thus, the frame structure 407 will hereinafter be referred to as a "gantry housing" in which the ring-gantry is housed. This gantry housing 407 comprises an internal space (not illustrated) which is configured to receive different functional parts of the bore based medical system.

Furthermore, the through-going bore 401 is configured to receive from the front side 403, a movable couch (not shown) configured to be moved into and out from the through-going bore 401.

Figure 15:
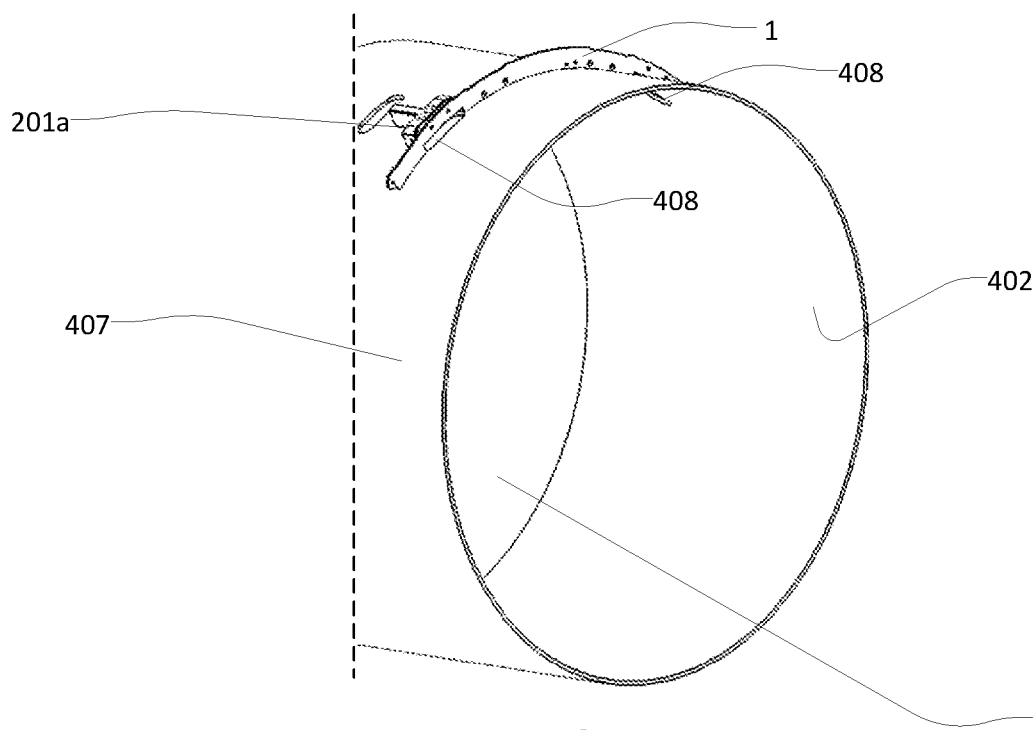
FIG. 15 illustrates a section of an inner side of the bore based medical system, wherein two treatment monitoring cameras are arranged on an internal frame side facing an internal space of the bore based medical system.

As illustrated in FIG. 10 and FIG. 15 two alternatives way of providing a camera carrier 1 in connection with the bore based medical system is illustrated. For purposes of this application, the term "camera carrier" is intended to encompass the combination of a radiotherapy beam source and the treatment monitoring camera(s) to be targeted at, and rotated around, the patient during the radiotherapy treatment, along with the gantry components (including rails) on which the aforementioned source and camera(s) are mounted.

Starting with FIG. 15, a first alternative is to mount a camera carrier 1 according to the disclosure within the internal space of the bore-based medical system. That is, in this embodiment, and as illustrated in FIG. 15, a camera carrier 1 is in one embodiment configured to be mounted on the bore wall defining the through-going bore 401. In this embodiment, illustrated in FIG. 15, surface 409 of the bore wall, opposite to the inner surface 402 (i.e., facing an internal space (not shown) of the gantry housing in which the gantry substantially rotates), is configured to have mounted thereon at least two treatment monitoring cameras 201a, 201b.

In more detail, the camera carrier 1 comprises at least two treatment monitoring cameras 201a, 201b mounted in connection with the inner surface 402 of the bore wall and together configured to cover a field of view including the iso-center focus point 23 (best illustrated in FIGS. 11 and 12) of the bore based medical system 400. The two treatment monitoring cameras 201a, 201b are configured to record images of a patient lying on the movable couch during radiotherapy treatment so as to allow monitoring and/or tracking of any motion performed by said patient.

As is apparent from FIG. 10, an alternative mounting of the two treatment monitoring cameras is to mount the cameras directly on a "bore facing part" of the gantry housing, i.e., the inner surface 402 of the bore wall. In any of the alternatives, the cameras are mounted within the bore and solves the problems of allowing surface guided radiotherapy, of especially breast cancer patients, when being treat with radio therapy. Mounting the treatment monitoring cameras internal to the bore allows for a sufficient field of view of record images of a patient or at least a part of a patient when lying within the through-going bore.

Accordingly, the configuration of the treatment monitoring cameras mounted within the bore, either integral to the internal space of the gantry housing (i.e., mounted on the previously mentioned surface 409 of the bore wall) and/or mounted the inner surface 102 of the bore wall allows the cameras to image a patient lying within the bore. The images recorded by the treatment monitoring cameras during e.g. radiotherapy treatment allows surface guided radiotherapy in a bore based medical system, which until now has not been possible. Such surface guided radiotherapy is especially relevant when treating breast patients in a bore based medical system, where it is necessary to be able to track the breathing of a patient during the treatment in order to avoid damage to healthy tissue around the tumor, when the breast of a person rises and fall during a breathing cycle. Such breast cancer treatments have not been possible in bore based medical system until now due to the lack of a camera system which provided a sufficient field of view of the patient within the through-going bore, and which is solved by the camera configuration, placement, and mounting as described herein.

Figure 16:
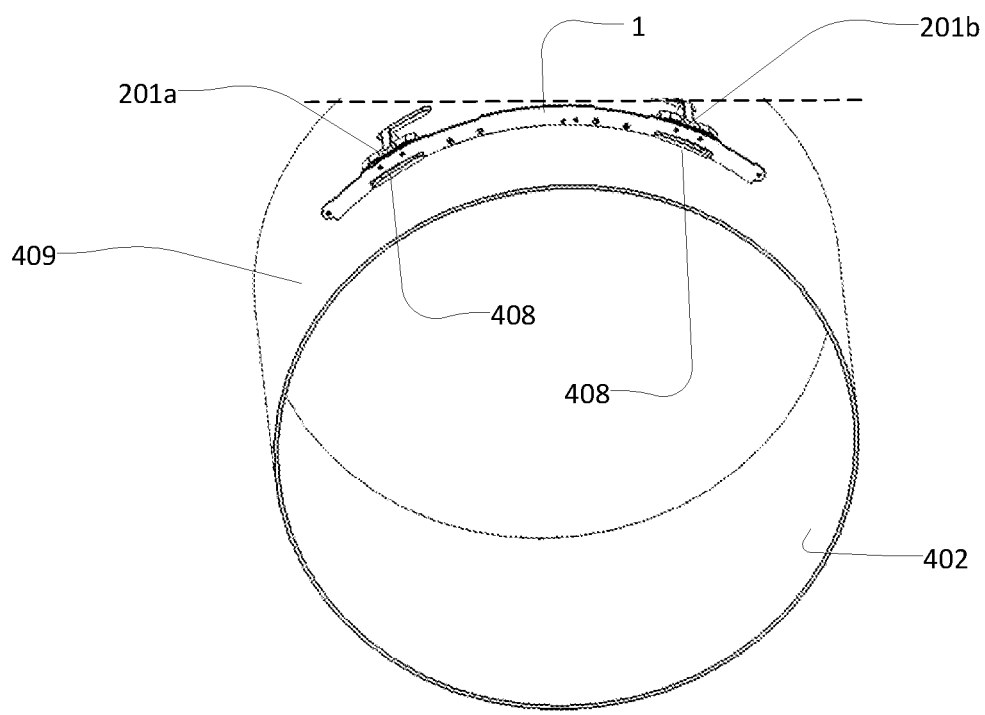
FIG. 16 illustrates a section according to FIG. 15 from a top view thereof.

In more detail, as illustrated in FIG. 15 and FIG. 16, the bore based medical system 400 comprises an internal space (not illustrated) of the gantry housing 407 between the bore wall and an opposing wall of the gantry housing 407 facing the internal space, wherein the rotatable gantry is configured to rotate within said internal space and said two treatment monitoring cameras are configured to be mounted within said internal space, wherein said bore wall comprises a transparent area, at a wavelength visible to cameras, 408 for each of said treatment monitoring cameras 201*a*, 201*b* allowing the treatment monitoring cameras 201*a*, 201*b* to record said images of the patient positioned within the field of view of the treatment monitoring cameras 201*a*, 201*b* at least covering the iso-center focus point of the bore based medical system.

It should be noted that in one embodiment, the transparent area 408 may also merely be a hole in the material of the bore wall through which the cameras 201*a*, 201*b* may be able to "look" out from. Thus, the lenses of the cameras (hereunder the camera viewing surface) does not need to be covered by a further layer of material when mounted integral to the inner side of the bore. Rather the "viewing surface" of the cameras may be substantially flush with the inner surface 402 of the bore wall.

In the embodiment according to FIGS. 15 and 16, where the two treatment monitoring cameras 201*a*, 201*b*, are integrated into the internal space of the gantry housing 407, e.g., mounted on the surface 409, it should be understood that if mounting the ring-gantry on the inner surface 402 of the bore wall illustrated in FIG. 10, one would be able to see each of the two treatment monitoring cameras beneath the material of the bore wall. Thus, one could say that in the alternative of FIGS. 15 and 16, the treatment monitoring cameras are arranged on an internal space of the gantry housing and, in the alternative of FIG. 10, the two treatment monitoring cameras are arranged external to the gantry housing but inside the through going bore. In any case, the camera construction and the mounting thereof is substantially the same, and will therefore be described in more detail in a common manner in the following. Thus, the following descriptions should be understood to be accountable for both alternative mountings of the treatment monitoring cameras.

Further in the following the camera carrier with at least two treatment monitoring cameras, will also be described to include further features in alternative embodiments. It should be understood that the two treatment monitoring cameras are necessary to solve the main problem of being able to track the patient during radiotherapy while the patient is lying on a couch within the bore, while the remaining features (among other two or more additional cameras) are options which could be added to the camera carrier to improve the surface guided tracking setup in a bore based medical system. In the following the camera carrier will thus be described in more detail in view of different embodiments which are combinable. The camera carrier will also be denoted as a carrier body through-out the description.

Camera Carrier Construction

Figure 1A:
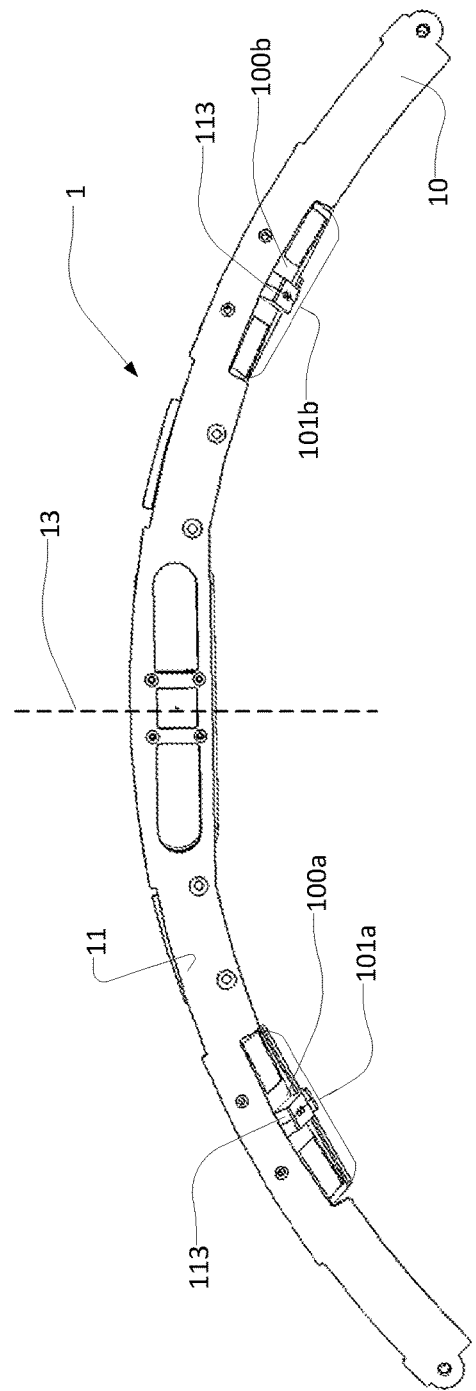
FIG. 1A illustrates a front view of an embodiment of a camera carrier according to the disclosure.
Figure 1B:
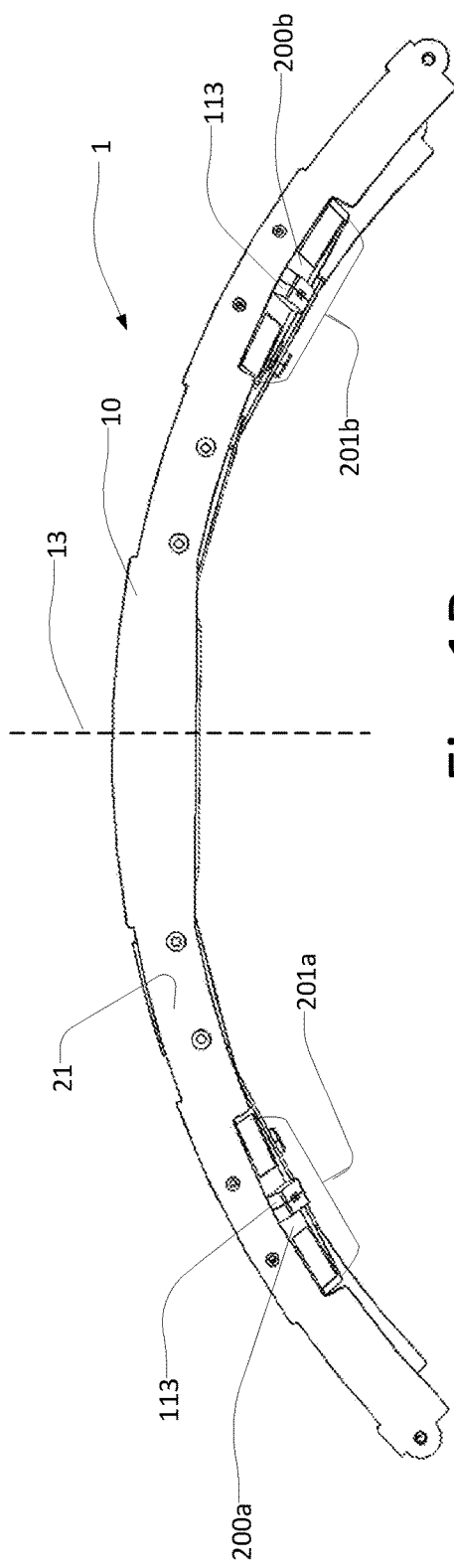
FIG. 1B illustrates a back view of the camera carrier of FIG. 1A.

Referring now to FIGS. 1A and 1B a front view and a back view, respectively, of the camera carrier 1 is illustrated in a first embodiment. The camera carrier 1 is configured to be mounted in a bore based medical system, as illustrated in e.g. FIGS. 10 and 11, where two examples of the camera carrier according to the Figures described herein, is illustrated.

As illustrated in FIGS. 1A and 1B the camera carrier 1 includes an at least partly ring-shaped body 10. The partly ring-shaped body should be construed as at least an arch which are formed in a manner so as to be inserted into a hollow bore of a bore-based medical system. The ring-shaped body 10 of the camera carrier 1 comprises two arch-shaped rails, i.e., a front body part 11 and a back body part 21, wherein the two arch-shaped rails (front body part 11 and back body part 21) are connected to form a width (w) (refer to FIGS. 2A and 2B) of the ring-shaped body 10. The ring-shaped body 10 furthermore comprises at least one front part camera 100*a*, 100*b*, which is at least one camera out of one or more cameras mounted in the ring-shaped body 10. In addition, the ring-shaped body 10 of the camera carrier 1 similarly comprises at least one back part camera 200*a*, 200*b* out of the one or more cameras mounted in the ring-shaped body 10. It should be noted that two front part cameras 100*a*, 100*b* and two back part cameras 200*a*, 200*b* are illustrated in FIGS. 1A and 1B, which is merely a preferred embodiment. Embodiments comprising only one front part camera 100*a* and one back part camera 200*a* could be contemplated.

The front part camera 100*a* and the back part camera 200*b* is as illustrated in FIGS. 1A and 1B configured to be mounted within the structure of the ring-shaped body 10, with camera viewing surfaces 101*a*, 101*b*, i.e. front viewing surface, and back viewing surfaces 201*a*, 201*b* facing a viewing area at opposite sides of the ring-shaped body 10.

In a preferred embodiment, as illustrated in FIGS. 1A and 1B, the ring-shaped body 10 comprises at least two front part cameras 100*a*, 100*b*, having a front viewing surface 101*a*, 101*b*, facing a front viewing area of the ring-shaped body 10, and the ring-shaped body on the opposing back-body part 21 comprises at least two back part cameras 200*a*, 200*b* having back viewing surfaces 201*a*, 201*b* (see FIG. 1B) facing a back view area of the ring-shaped body 10. As illustrated in FIG. 1A the two front part cameras 100*a*, 100*b* are mounted in the ring-shaped body 10, at an equal distance from a symmetric line 13 of the partly ring-shaped body 10. Similarly, as illustrated in FIG. 1B, the two back part cameras 200*a*, 200*b* are also mounted at an equal distance from the symmetric line 13 of the partly ring-shaped body 10.

Turning now to FIG. 2A, which illustrates a top view of the camera carrier 10 according to FIG. 1A and FIG. 2B which illustrates a bottom view of the camera carrier 1 according to FIG. 1B, the construction of the camera carrier 1 and the front part camera 100*a*, 100*b* and back part camera 200*a*, 200*b* mounted thereon is illustrated in more detail. As can be seen the ring-shaped body 10 comprises a first substantially back-to-back camera configuration 12a, wherein the first front part camera 100a is mounted substantially back-to-back with the first back part camera 200a. Further, at an opposite side of the symmetric line 13, as explained in relation to FIGS. 1A and 1B, a second back-to-back camera configuration 12b is arranged within the ring-shaped body 10, wherein the second front part camera 100b is mounted substantially back-to-back with the second back part camera 200b.

To enable viewing surfaces 101a, 101b, 201a, 201b to transfer incoming light to an image sensor internal to the cameras, the front part cameras 100a, 100b is configured with internal camera mirrors, which is angled in relation to said front viewing surfaces 101a, 101b and the back part cameras 200a, 200b is similarly configured with internal camera mirrors angled in relation to the back viewing surface 201a, 201b. It should be noted that the "viewing surface" should be construed as the surface of the cameras at which reflected light from a target enters into the cameras. Within the cameras the mirrors are oriented to reflect the light onto a lens, which then transfers the light onto an image sensor in a standard manner. A more detailed description of these internal camera parameters and the construction thereof will in an embodiment be described in relation to FIGS. 6 to 9.

Figure 7:
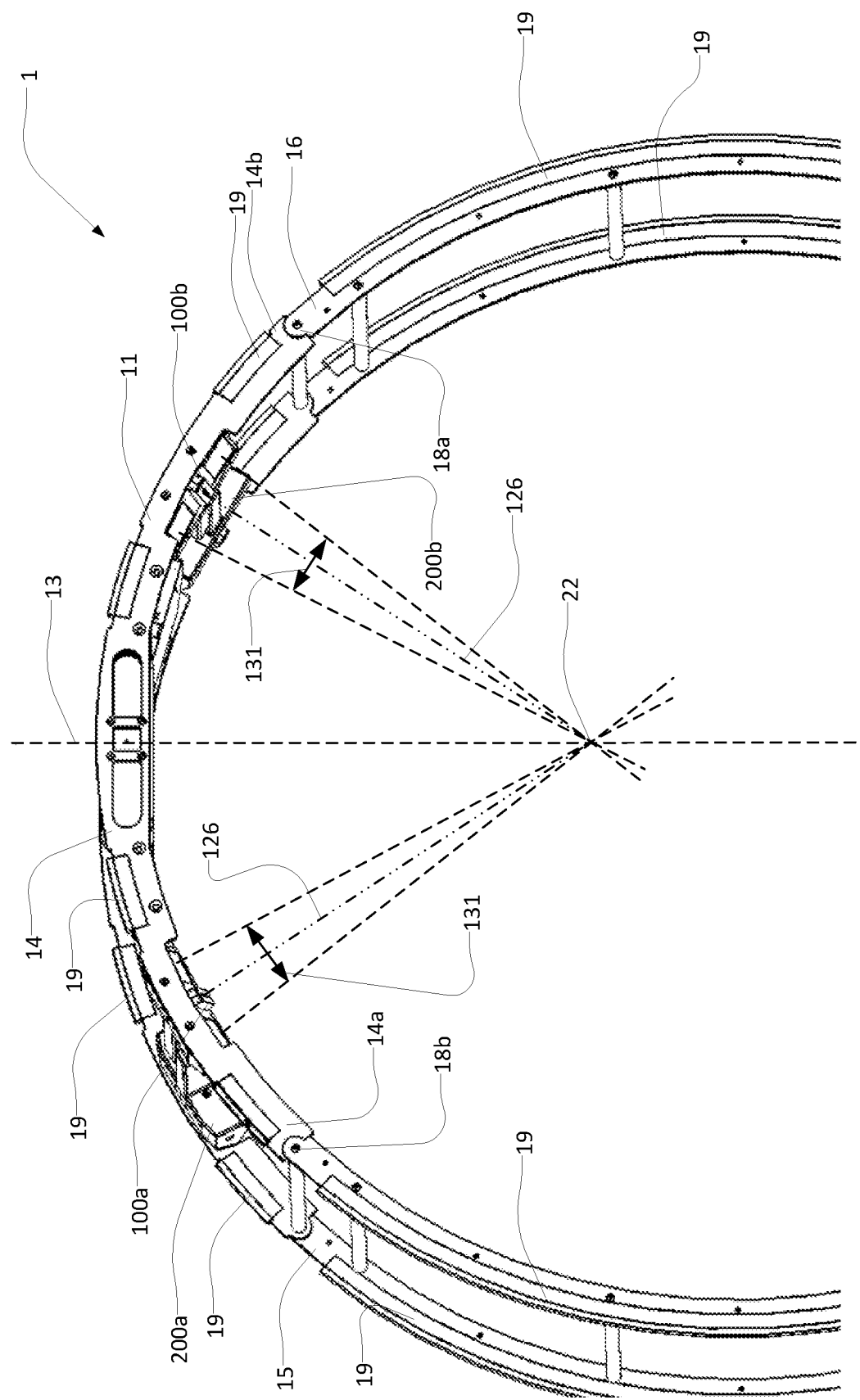
FIG. 7 illustrates an embodiment of a camera carrier according to the disclosure.

In embodiments described herein, each of the first and second front and back part cameras may comprise a projector 113 configured to project a light onto a target configured to be arranged within a field of view of one or more cameras. Such projector 113 is as illustrated in FIG. 1A for the front part cameras 100a, 100b, and FIG. 1B for the back part cameras 200a, 200b, configured as a small projection extending outwards from the viewing surfaces 101a, 101b, 201a, 201b of each of the front 100a, 100b, and back part cameras 200a 200b, respectively. Please note that a "field of view" in the context of the disclosure should be construed as the extent of the observable world that is seen at any given moment by mirrors of the cameras, i.e. as illustrated in FIG. 7, as the field of view 131.

As is apparent from the Figures, the front part cameras 100a, 100b and the back part cameras 200a, 200b in a preferred embodiment have the same camera construction. Thus, to ease the understanding of the internal camera construction covering these mentioned cameras of the camera carrier 1, reference is made to FIGS. 3 to 6.

Figure 3:
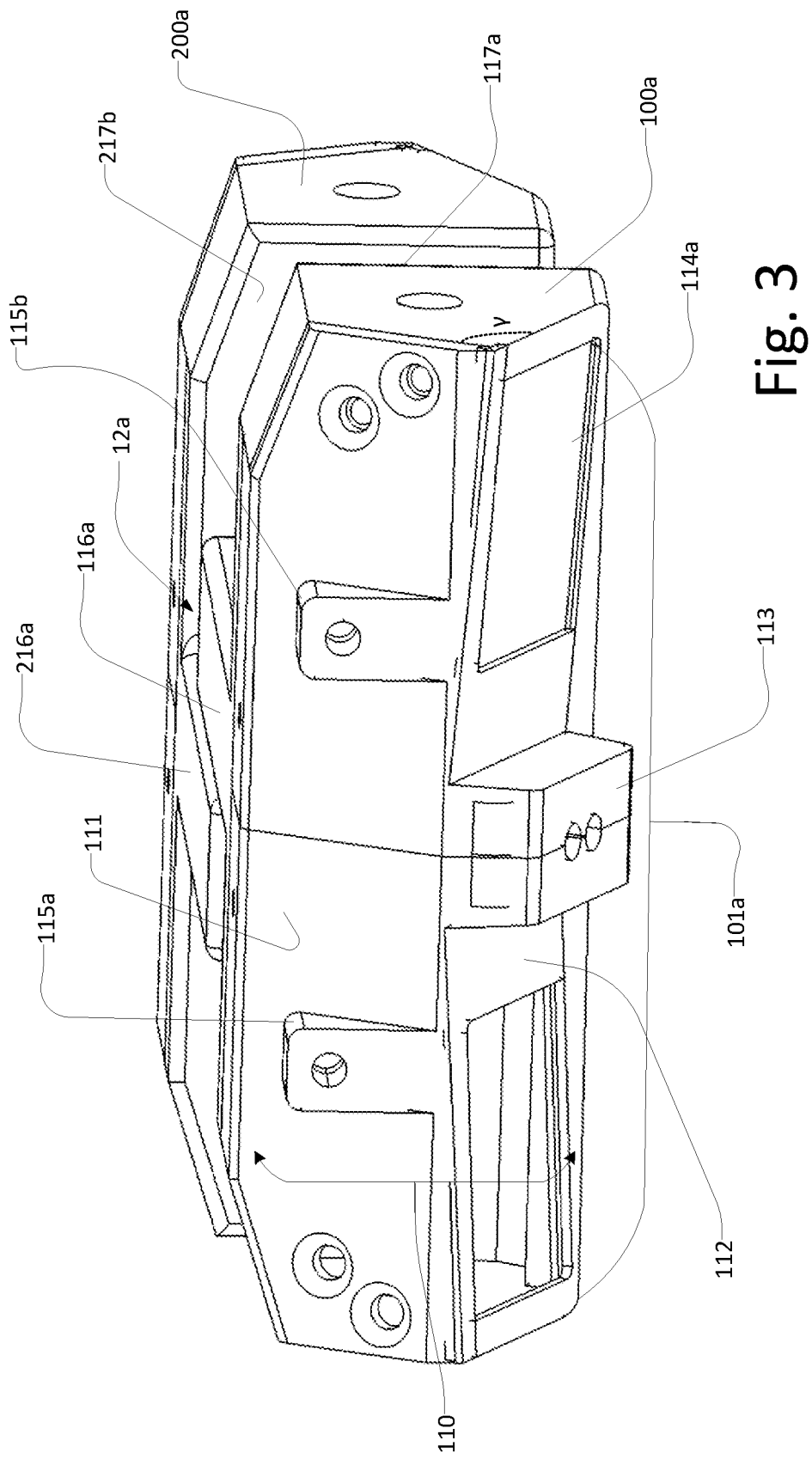
FIG. 3 illustrates a representative example embodiment of the front part cameras and the back part cameras of FIG. 1 in an embodiment of the disclosure.

Initially starting with FIG. 3, a front view of an example of a back-to-back camera configuration 12a, 12b in accordance with FIGS. 2A and 2B, is illustrated. This back-to-back configuration could be any of the first back-to-back configuration 12a or the second back-to-back configuration 12b.

As is seen the back-to-back configuration 12a, 12b comprises a front part camera 100a which is oriented substantially back-to-back with a back part camera 200a in accordance with e.g. the embodiment of FIGS. 2A and 2B. The front part camera 100a is used as an example to explain the camera construction suitable for all front part and back part cameras described herein. Accordingly, the front part camera 100a (and equally the back part camera 200a, second front part camera 100b and second back part camera 200b) comprises a front surface 110 which is configured with a camera mount surface 111 and a second surface 112 comprising the front viewing surface 101a. As seen in FIG. 3, the second surface 112 with the front viewing surface 101a, is angled with an angle γ in relation to the camera mount surface 111. This enables that two filters 114a, 114b (only one shown) are facing downwards towards a focus point 22, exemplified by the focus point for the front part cameras (refer to FIG. 7) of the camera carrier. Further in FIGS. 2A and 2B, a camera hub 129 is illustrated, which is configured to synchronize all the cameras and to distribute signals to and from each of the cameras together with providing power to the cameras. Thus, all cameras are electrically connected with the camera hub 129. Please note that other embodiments illustrate two camera hubs as an example, but preferably only one is necessary.

As also seen in FIG. 3, the previous mentioned projector 113 is configured to be arranged at the second surface 112 enabling a projector, which is angled to have a field of view 126 (illustrated by a single line within the field of view 131 of the cameras) towards the focus point 22 of the camera carrier (refer to FIG. 7).

Furthermore, in the example embodiment illustrated in FIG. 3, two camera fixing elements 115a, 115b is forming part of the camera mount surface 111. These fixing elements 115a, 115b is utilized to enable the cameras to be mounted to the front body part and/or back body part of the ring-shaped body 10 as illustrated in FIG. 2A.

It should be noted that the fixing elements in an embodiment may also be arranged on top parts of the cameras, such as e.g. on the backward extending parts 116a, 216a of the cameras illustrated in e.g. FIG. 3. In this way the fixing of the cameras may be from a top part of the camera to the ring-shaped body. Other alternative ways of attaching the cameras to the ring-shaped body is possible and would be considered by a skilled person.

In relation to the back-to-back configuration as defined throughout the disclosure, this should be understood to be a configuration, wherein at least a part of a back side of the front part camera and at least a part of a back side of the back part camera substantially abut each other. As illustrated in an example in FIG. 3, this could be e.g. the backwards extending parts 116a and 216a of the front part camera 100a and back part camera 200a, respectively, that abut each other. In an alternative embodiment (not illustrated) these backwards extending parts 116a, 216b could be the back surfaces 117a, 217b of the front part camera 100a and back part camera 200a, respectively, that abut each other.

Figure 4:
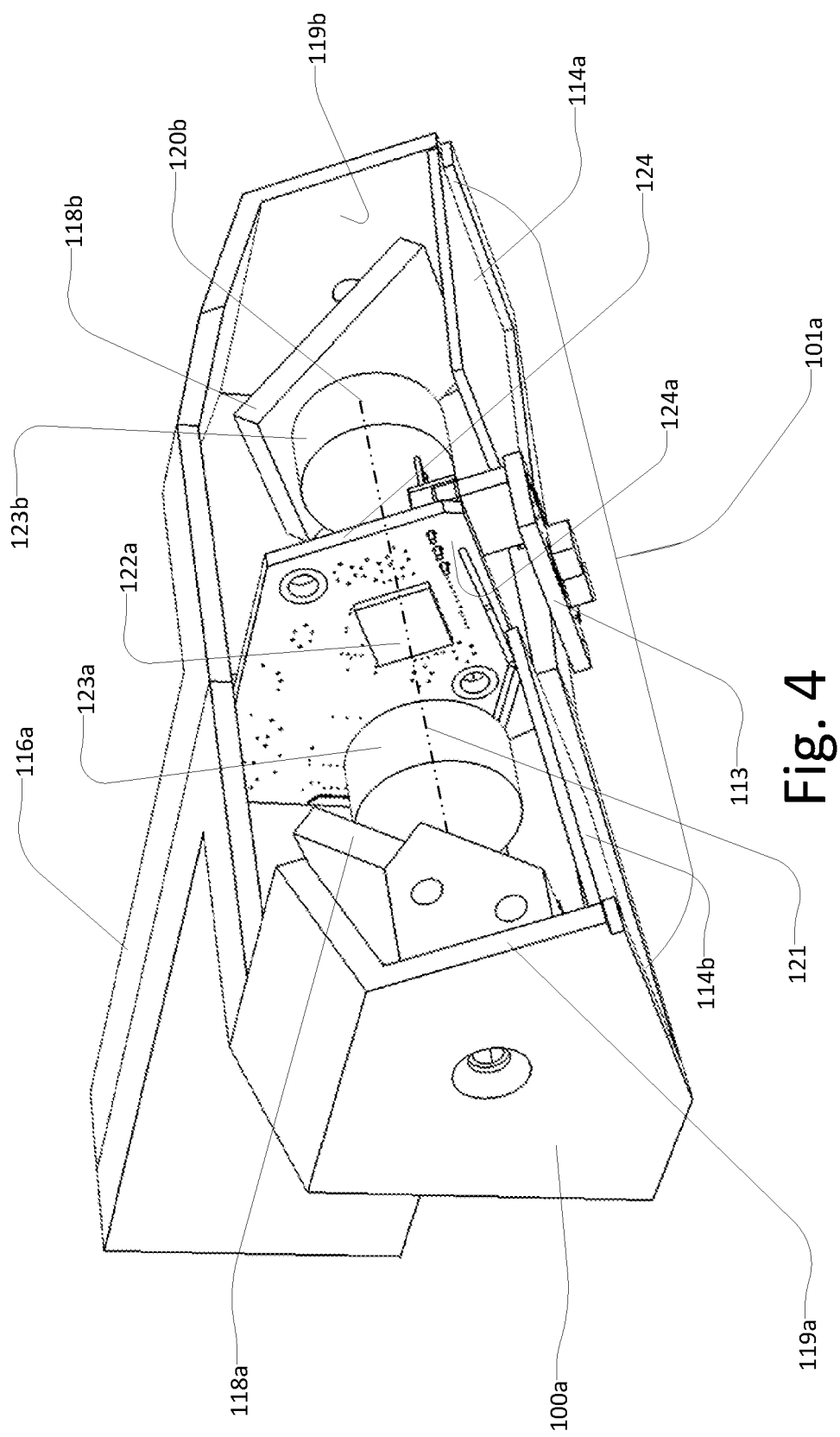
FIG. 4 illustrates a perspective partly side view of the camera in FIG. 4, where a front surface of the camera has been left out.

Turning now to FIG. 4, the internal parts of the front part and back part cameras will be described in more detail. Again, the front part camera 100a will be provided as an example, and it should be noted that the described features also forms part of the second front part camera 100b, the first back part camera 200a, and the second back part camera 200b.

In FIG. 4, the front part camera 100a is illustrated in a perspective view with at least some parts removed. Thus, as illustrated the camera mount surface 111 of the front surface 110 as illustrated in FIG. 3 is removed thereby allowing a view of at least parts of the internal components of the cameras. As illustrated, the camera 100a comprises the previous described filters 114a, 114b together substantially defining the front viewing surface 101a.

Figure 5:
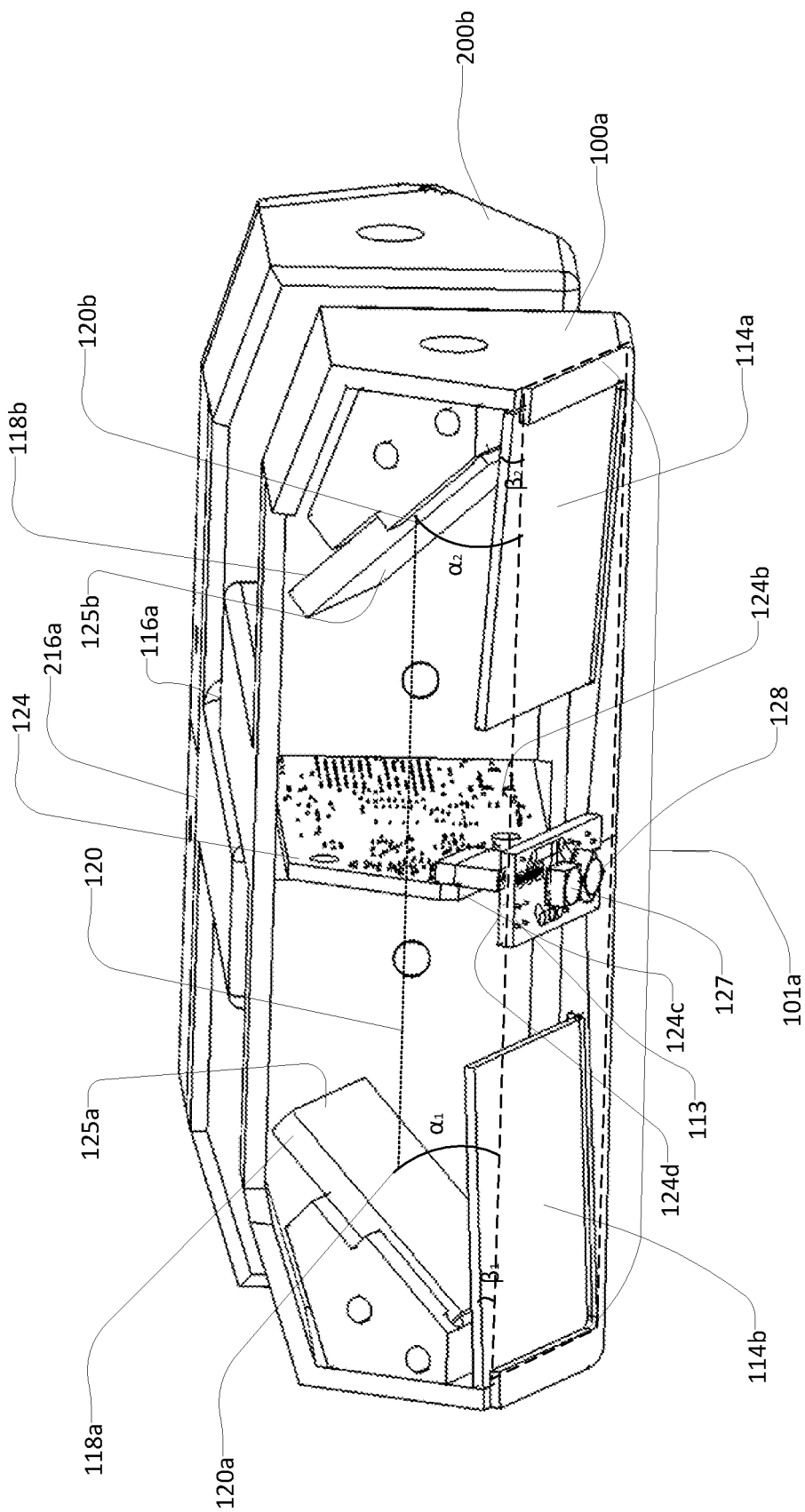
FIG. 5 illustrates a perspective front view of the camera in FIG. 4, where parts of the camera has been left out.

Furthermore, the cameras comprises at least two internal mirrors 118a, 118b, wherein a first mirror 118a is arranged at a first end surface 119a of the camera and a second mirror 118b is arranged at a second end surface 119b of the camera, wherein each of the mirrors 118a, 118b comprises a mirror center 120b (illustrated by a small dot on the mirror) and wherein a mirror center axis 121 (refer also to FIG. 5) is defined between said mirror centers 120a, 120b (refer to FIG. 5 for an illustrated of both mirror centers).

As further illustrated in FIG. 4, the camera 100a comprises a first lens 123a and a second lens 123b arranged at opposite side areas at a distance from a substrate 124 holding among other components, the electronic components of the camera. The substrate 124 furthermore comprises an image sensor configuration, where a first image sensor 122a is mounted on a first side 124a of the substrate 124, and a second image sensor (not shown) is mounted on a second side 124b of the substrate 124 (refer to FIG. 5 for the second side).

These internal camera features might be considered substantially standard features of a camera, however, for the cameras to have the correct field of view when arranged on a substantially ring-shaped body 10 to be mounted in a bore-based medical system, where the camera body is substantially parallel to the centerline of the bore, it is important that the orientation of the elements, i.e. angle relationships between mirrors, lenses and sensors is suitable for a substantially "arched" (i.e. partly ring-shaped) construction. Thus, the inventors have carefully considered these relationships, and have found that for such camera construction to be mounted in an arch and substantially cover the needed focus points of a bore based medical system and to maximize the distance to the object imaged in the bore, the internal mirrors 118a, 118b may in a preferred embodiment illustrated as in e.g. FIG. 5.

Here the mirrors 118a, 118b are arranged so as to form a mirror angle $\alpha_1$, $\alpha_2$ between a mirror plane 125a, 125b and the plane of the viewing surface 101a (illustrated by a dotted line within the brace marked by 101a), wherein the mirror angles $\alpha_1$, $\alpha_2$ are configured to be at least 45 degrees or above in order for the field of view from each sensor converges. As further illustrated in FIG. 5, the filters 114a. 114b are also angled with an angle 131, (32 to the viewing surface 101a, where the angle $\beta_1=\beta_2$. In more detail, the relationship between the mirror angles $\alpha_1$, $\alpha_2$ and the filter angles are $\beta_1$, $\beta_2$ is preferably given by $$\beta_1,\beta_2=2*(45°-\alpha_1,\alpha_2)$$

With this constructional relationship between the mirrors, filters and the viewing angle it is ensured that the cameras is provided with a sufficient field of view of covering a target area in the ring-shaped body, when the ring-shaped body is inserted into the bore of a bore-based medical system. Further such angling of the mirrors together with the sensor orientation as described in the following allows for the cameras to be positioned in the camera ring, with the top surface (exemplified by the backwards extending parts 116a, 216a) of the cameras substantially parallel with a centerline of ring-shaped body.

Accordingly, and as previously mentioned and further illustrated in FIG. 4 to FIG. 6 and explained in the following, the cameras 100a (and also 100b, 200a, 200b) may comprise at least a first image sensor 122a configured to be arranged on the substrate 124 of the camera at a distance from the first mirror center 120b, and a second image sensor (not shown) configured to be arranged at an opposite side of the substrate 124 than the first image sensor 122a at a distance from a second mirror center 120a, wherein a mirror plane 125a, 125b of each of the first mirror 118a and second mirror 118b are configured to be oriented at an angle $\alpha_1$, $\alpha_2$ in relation to the plane of the viewing surface 101a of said camera, wherein $\alpha_1$ equals $\alpha_2$.

Figure 6:
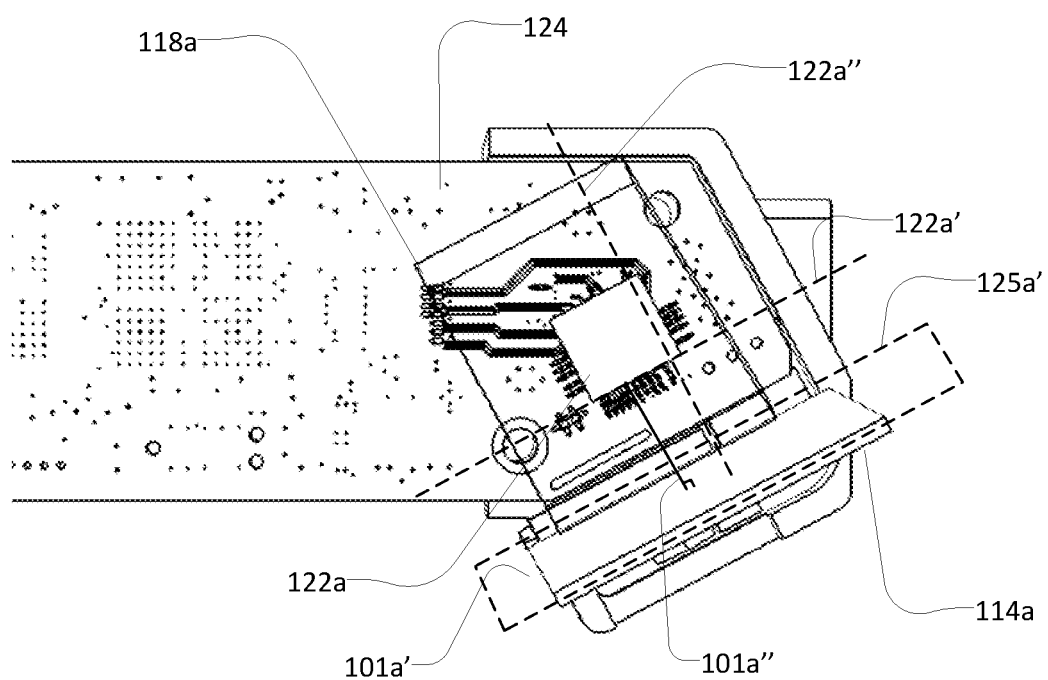
FIG. 6 illustrates a side view of internal parts of the camera in FIG. 4.

Furthermore, the first image sensor 122a (and also the second image sensor) comprises a first sensor axis 122a' and a second sensor axis 122a" perpendicular to the first sensor axis 122a', wherein, as illustrated in FIG. 6, at least one of the first sensor axis 122a' or the second sensor axis 122a" is arranged normal 101a" to the plane 101a' of the viewing surface 101a and parallel with a first mirror axis 125a' of said mirror plane 125a. In this regard reference is made to FIG. 6, where all the above mentioned axes have been illustrated and provided with a number to enable correct understanding of the internal construction of the camera. Especially, the sensor orientation in view of the plane 101a' of the viewing surface is considered to be important by the inventors, since it allows the camera body to be arranged parallel with a center line of the bore.

In other words, the first mirror axis and the first or second sensor axis could also be said to be arranged in parallel with an axis of the plane 101a' of the viewing surface 101a. This construction allows that the working distance from the camera to a subject oriented within the field of view of the cameras is maximized. If the image sensor had been mounted conventionally, the whole camera would need to be tilted to achieve the same effect, and as a result offset by the camera length times the sine of the tilt angle, which would reduce the working distance. In the restricted space of a bore in a bore based medical system, this construction represents a significant increase in working distance. One of the benefits of the construction described herein, is that occlusions is reduced with working distance, and field of view increases for a given lens focal length. Working closer with a shorter focal length increases occlusions and means greater lens distortion attributed to very short focal length lenses.

Accordingly, with this internal construction of the cameras, it is ensured that the cameras can be mounted in an arch shaped (i.e. partly ring-shaped camera carrier) while allowing the cameras to cover a field of view which covers a wanted target area in a bore-based medical system, as will be described in greater detail in later parts of the disclosure. In other words, the arrangement of the front part camera and back part cameras together with the internal construction of these cameras (as explained in relation to an example front part camera), ensures that the front part cameras and back part cameras are looking at the same object with the same angles, but looking from opposite directions towards the object. Thus, sufficiently covering a setup focus point and a treatment focus point, respectively, of the bore-based medical system.

Referring now to FIG. 7, the camera carrier 1 is illustrated in an embodiment, wherein the front part cameras 100a, 100b, and back part cameras 200a, 200b previously described are mounted in a ring-shaped body 10 of the camera carrier. As illustrated in FIG. 7, and as previously described in relation to FIG. 1A, 1B, the front part cameras 100a, 100b, and back part cameras 200a, 200b are arranged substantially symmetrically in the ring-shaped body 10 at an equal distance form a symmetric line 13 of the ring-shaped body 10. This arrangement in the ring-shaped body 10 together with the internal construction of the cameras as just described enables that the first front part camera 100a and the second front part camera 100b covers the same field of view thus allowing a target positioned within the field of view of the cameras to be efficiently seen by the cameras. This "target position" could also be defined as the front facing focus point 22 of the ring-shaped body. Thus, in other words, the ring-shaped body 10 may comprise a front focus point 22 (and/or a back focus point for the back part cameras), wherein the first back-to-back camera configuration 12a, and the second back-to-back camera configuration 12b is arranged in or on the ring-shaped body at a substantial identical radial distance and field of view angle from the focus point.

In more detail, the camera carrier may with its front part cameras 100a, 100b and back part cameras 200a, 200b comprise at least two different focus points. That is, the front part cameras 100a, 100b have a viewing plane facing substantially below and to the front of the camera carrier, whereas the viewing plane of the back part cameras 200a, 200b is substantially mirrored to those of the front part cameras, thus creating a second viewing plane facing substantially below and to the back of the camera carrier. Thus, the camera carrier can be said to be constructed with a field of view of the front part cameras intersecting at a setup focus point of said camera carrier, and with a field of view of the back part cameras 200a, 200b intersecting a treatment focus point of the camera carrier. This is especially relevant to bear in mind in view of correct placement of the camera carrier in a bore based-medical system, as will become apparent.

Referring again to FIG. 7, the camera carrier 1 is illustrated in an embodiment of the disclosure, wherein the camera carrier 1 is formed as a ring-shaped body, and not only, as in the previous described Figures, as a partially ring-shaped body, such as an arch. As is seen in FIG. 7, the camera carrier 1 comprises the arch piece as described in relation to FIGS. 1A to 2B, where the front part cameras 100a, 100b and back part cameras 200a, 200b are mounted on this first arch piece of the fully ring-shaped body. It should be noted that the "first arch" illustrated in FIG. 7 corresponds to the arch of the ring-shaped body 10 as described in relation to FIGS. 1A to 2B. Furthermore, the cameras are the same as those describes in relation to FIGS. 3 to 6.

Figure 9:
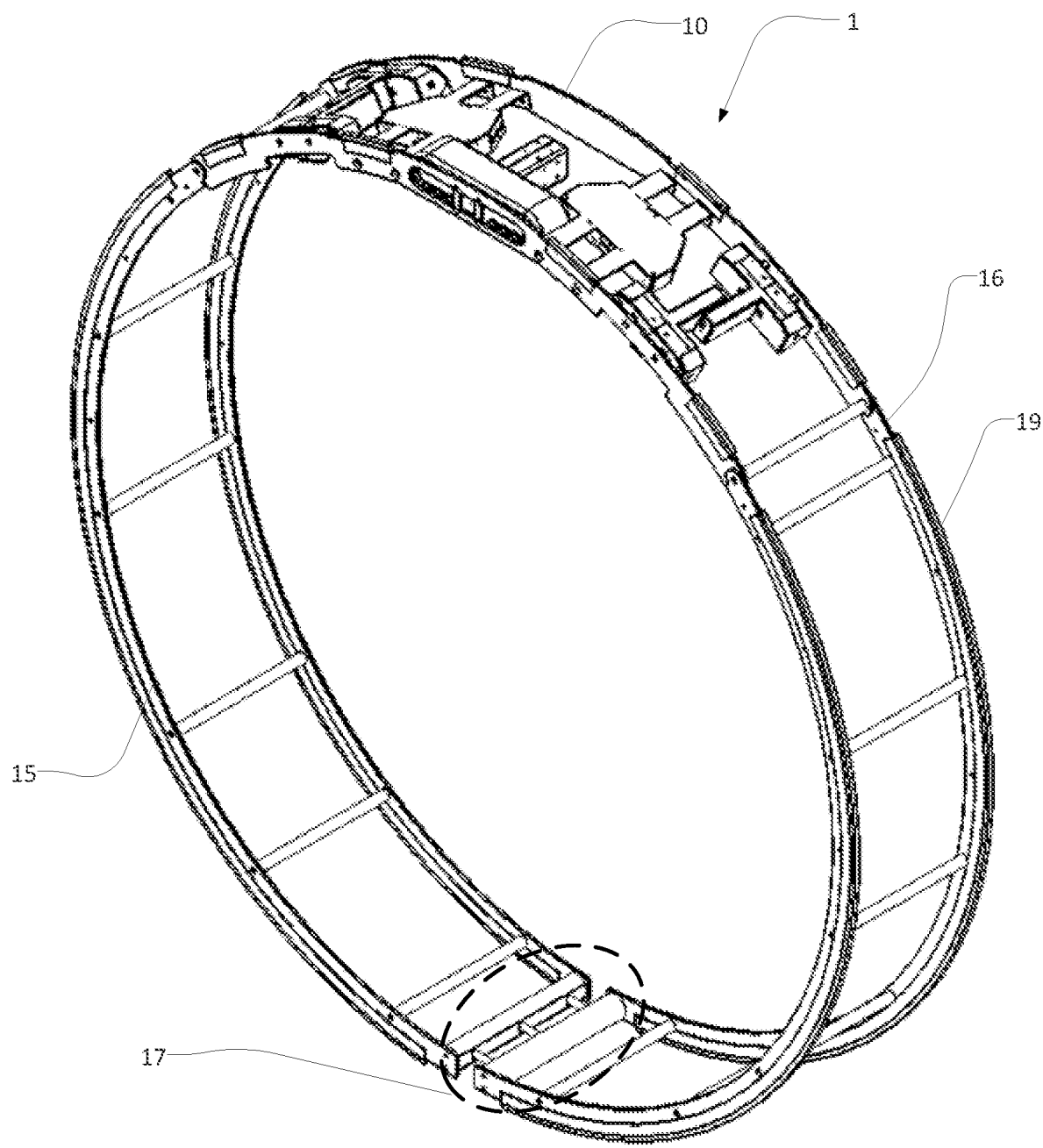
FIG. 9 illustrates an embodiment of the camera carrier according to FIG. 7, where the camera carrier further comprises the third front camera.

In more detail, the camera carrier 1 illustrated in FIG. 7 and FIG. 9 comprises the first arch 14, which in a first end 14a is configured to be connected to a left arch 15 and in a second end 14b is configured to be connected to a right arch 16. As illustrated in FIG. 7, each of the left 15 and right 16 arches are connected via a substantially flexible joint 18a, 18b to the first arch 14. The left 15 and right 16 arches is further connected to each other through an adjustable expansion element, wherein the expansion element is configured to be adjusted to a first expansion stage forcing the left 15 and right 16 arches away from each other and a second stage relieving the first expansion stage. Accordingly, when the ring-shaped camera carrier 1, 10 is mounted in a bore based medical system as described herein, the left 15 and right 16 arches (also denoted sides) are pushed apart which forces the flexible joints 18a, 18b to allow the left 15 and right 16 arch to rotate in relation to the first arch 14, thereby allowing a circular shape of the ring-shaped camera carrier 1. By this rotation of the arches 15, 16 via the flexible joints 18a, 18b, the ring-shaped camera carrier may form a ring-shaped structure corresponding to the inner side of a bore-based medical system. The expansion element 17 allows a constant push-force on the arches 15, 16 forcing the arches and thus the ring-shaped structure to stay in place when mounted in the bore-based medical system. It should be noted that the ring-shaped structure is preferably held in place in the bore-based medical system by frictional forces.

Accordingly, in an embodiment, it should be noted that once the first 14, left 15 and right 16 arches are joined, the three arches together form a circle (i.e. a ring) for which the outside diameter is the same as the internal diameter of the bore of the bore-based medical system.

To ensure a high friction interface between the inner side of the bore of bore-based medical system and the outer sides of the camera carrier 1, the camera carrier comprises at least at parts thereof, a gasket mounted on an outer periphery of the camera carrier. This is illustrated on e.g. FIG. 7, where the gasket parts are denoted 19. As can be seen from FIG. 7, the gasket in this embodiment only covers parts of the outer periphery of the camera carrier, however, this should not exclude the possibility of applying a continuous gasket covering the full periphery of the ring-shaped camera carrier 1. Furthermore, the rubber gasket is configured to dampen external vibrations that may be transferred from third party equipment to the bore.

Thus, the solution may in a preferred embodiment form a ring (i.e. ring-shaped body) that is inserted inside a bore of a bore-based medical system and is held in place by a substantially outwards force towards the bore (i.e. via the expansion element). This avoids having a complex mounting structure to hold the camera carrier in position and at the same time applies minimal force on the bore structure. The gasket, such as a soft rubber gasket, is used between the camera "ring" and the bore to ensure a high friction interface to the bore.

Referring now to FIG. 5, an example embodiment of the projector arrangement within the cameras will be explained. Again, the front part camera 100a is taken as an example, and it should be understood that the projector is arranged in a similar manner in the second front part camera 100b, the back part camera 200a, and second back part camera 200b. As is illustrated the projector 113 is arranged to be connected with the substrate 124 (i.e. PCB) at a lower side part 124c of the substrate. As illustrated in FIG. 5, the projector 113 comprises a first projector 127 and a second projector 128. These may be configured as dual dot projectors, such as a pair of commercially available dot projector VCSEL devices. These projectors are arranged in the cameras to sufficiently suit a 3D reconstruction camera. Accordingly, the unique arrangement of the projectors is such that the projectors are arranged on a projector PCB 124d connected with the main substrate 124 in such a manner that the first projector is rotated 45 degrees in relation the second projector. This is illustrated clearly in FIG. 5, where it is seen that the two projectors are angled in relation to each other with an angle $\beta$. The preferred angle $\beta$ is 45 degrees, however angles rotation between the two projectors could be chosen from the ranges $0°<\beta<90°$, $90°<\beta<180°$, $180°<\beta<270°$, $270°<\beta<360°$. By rotating one of the first or second projectors in relation to each other with the angle $\beta$, it is ensured that the projected pattern is locally unique and makes 3D reconstruction of the recorded object more reliable and robust. That is, the pattern is regular, where using two projectors means there is more detail in the pattern. Locally there is no repletion but over a larger area the pattern will repeat. This can impact seed pointing for stereo (initially finding similar portions in the image). When two cameras project onto the surface this adds even more variation to the projected pattern. It should be noted that the dual dot projector arrangement as illustrated in FIG. 5, can be implemented in any other suitable way for aiding 3D reconstruction, and this description should therefore only be contemplated as an example.

Couch Monitoring Camera

Figure 8:
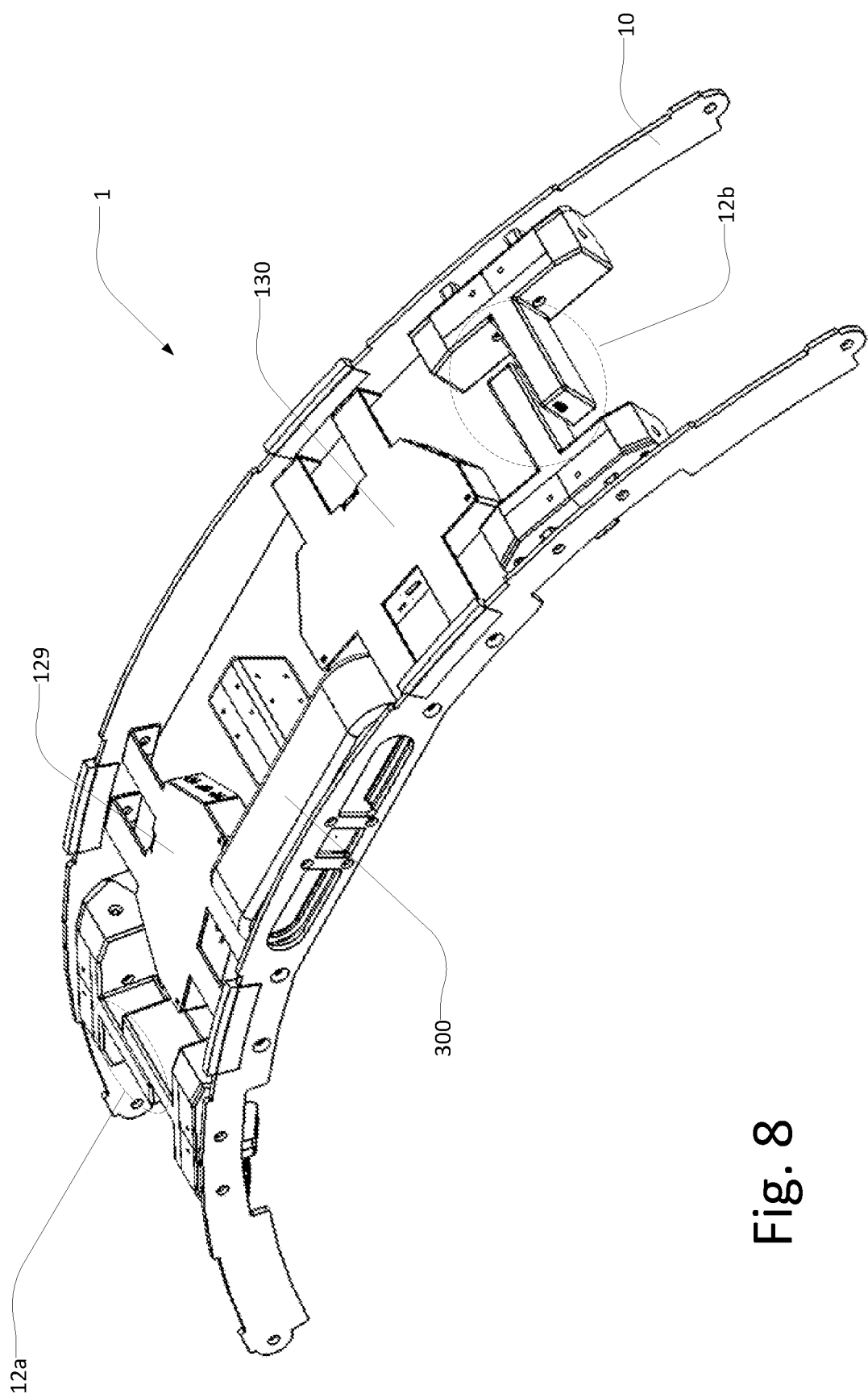
FIG. 8 illustrates an embodiment of a camera carrier according to FIGS. 1B and 1A, where the camera carrier furthermore comprises a third front camera.

Referring now to FIG. 8, an embodiment showing a camera carrier 1 with a further camera is illustrated in a side perspective view. The illustrated embodiment corresponds to the camera carrier structure as described in relation to FIGS. 1A to 2B, where a further third front camera 300 is mounted in the ring-shaped (substantially arch shaped) 10 body of the camera carrier 1.

As is seen, the third front camera 300 is arranged substantially mid-centered in relation to the first back-to-back camera configuration 12a and the second back-to-back camera configuration 12*b*, wherein the third front camera 300 is configured with a lens orientation having a field of view covering at least a part of a couch of said bore-based medical system in a mounted state of the ring-shaped body.

Accordingly, in the embodiment shown in FIG. 8, the camera carrier comprises at least five cameras, wherein two cameras (i.e. the two front part cameras 100*a*, 100*b*), are configured to cover a field of view containing a patient positioned on a couch in a setup stage when the camera carrier 1 is mounted in a bore-based medical system, two back part cameras 200*a*, 200*b*, which are configured to cover a field of view containing a patient positioned on a couch in a treatment stage, when the camera carrier 1 is mounted in a bore-based medical system and one mid-centered front camera 300 which is configured to monitor a couch or e.g. a marker on a couch of the bore-based medical system, when the camera carrier 1 is mounted in a bore-based medical system. Accordingly, the mid-centered camera is substantially configured to monitor the couch of the bore-based medical system and is therefore also referred to as the couch monitoring camera.

In more detail, the couch monitoring camera may comprise a near infrared illuminator, such as an LED. The near infrared illuminator is configured to illuminate e.g. retroreflective markers in the treatment room of the bore-based medical system. The retroreflective markers could e.g. be positioned on the couch of the bore-based medical system to allow the couch monitoring camera to monitor any movement of the couch. Thus, the near infrared illuminator may be configured to be pulsed in time with the sensor exposure, which minimizes power consumption and therefore minimizes heat output from the LED.

In another example embodiment, the couch monitoring camera may be configured without the infrared illuminator, and instead record a signal from e.g. active markers on for example the couch of the bore-based medical system.

In yet a further example embodiment, the couch monitoring camera may be configured to track an object positioned on or at least in connection with the couch.

In general, the couch monitor camera is configured to monitor the couch movement in all directions to allow a tracking of a patient positioned on the couch, so as to evaluate if e.g. the patient and or the couch has moved in relation to the setup focus point and/or e.g. the iso-center focus point of the bore-based medical system. That is to ensure that the front and back part cameras can compensate for any couch movement when generating a 3D surface of a patient positioned on the couch. Further, the couch monitor camera may also be configured in an embodiment to independently verify the motion of the couch.

Referring now to FIG. 9, the fully ring-shaped camera carrier 1, as also explained in relation to FIG. 7, is illustrated in a perspective front view of the camera carrier 1. The camera carrier comprises the features previous explained in relation to FIG. 8, and furthermore, the expansion element 17 is illustrated. The left 15 and right 16 arches is as illustrated more clearly on FIG. 9 connected to each other through an adjustable expansion element 17, wherein the expansion element 17 is configured to be adjusted to a first expansion stage forcing the left 15 and right 16 arches away from each other and a second stage relieving the first expansion stage. As also seen in this embodiment, the gasket 19 (or gasket components all denoted 19) is configured to cover at least parts of the ring-shaped body on an outer periphery thereof.

It should be noted that the cameras and the ring-shaped body described herein are preferably made from a lightweight construction, such as composite material and/or aluminum allowing a minimal load on the bore, when mounted into a bore-based medical system. In general, the material and profile of the ring-shaped body is chosen so as to have as less impact on the dosage from the radiotherapy gantry as possible.

Furthermore, the third front camera, should be considered as a couch monitoring camera, which is substantially configured as a stereo vision camera, optionally featuring a near IR LED(s) to illuminate markers on for example the couch of a bore based medical system. The couch monitoring camera (also denoted the third front camera) is configured to track any couch movement, sag etc, that may occur and which can influence the accuracy of the further processing of images recorded by the cameras of the ring carrier. In an embodiment, the third front cameras is therefore configured to track markers on the couch, which markers could be active in which case no illumination from the third front camera would be required. In another example embodiment, the third front camera is configured to track a structure or shape on the couch that has uniquely identifiable features, for which a Centre of Gravity or Centroid can be determined. Another variant would be for the Couch monitoring camera to monitor the end of the couch that protrudes into the bore. This would be able to track couch motion and couch sag. The couch monitoring camera avoids the need for any integration with third party equipment, instead at the time the patient is set up to the reference position in the setup stage the couch location is recorded. All subsequent couch movements can then be tracked, so when the couch is moved from the setup location (Room or External Isocentre) to the treatment position the precise shift in 3D space can be estimated.

Referring now to FIG. 8 (or similarly FIGS. 2A and 2B) it is illustrated that the camera carrier 1 may further in an embodiment comprise one or more camera hubs 129, 130, which is substantially configured with electronic components configured to allow communication between the cameras, the bore-based medical system and processing units configured to process the data recorded by the cameras. The camera hubs 129, 130 is configured to allow synchronization of the first and second front part camera and the first and second back part camera. The camera hubs 129, 130 comprises standard USB-C cables, which is configured to be used for synchronizing the cameras. USB-C incorporates interconnect for connection of monitors, microphones and other peripherals, these are Sideband Use signals (SBU1 & SBU2). These Sideband Use signals are used to provide specific functions to cameras used in this environment, specifically camera synchronization and a mute signal for an illumination system, such as the dual dot projector 113, used by cameras. The cameras may be configured as one master and a plurality of slave cameras, or as all slaves where the synchronization signal is generated by a camera control unit or an external system. Similarly, a signal to mute the projector can be controlled by a chosen master camera of the one or more cameras of the camera carrier, or a camera control unit, which can generate the signal itself or pass it from an external system. Please note that FIG. 8 illustrates an embodiment where two camera hubs are present, however, it should be noted that only one hub could also be used and therefore at least one of the illustrated camera hubs in FIG. 8 can be left out (see also embodiment in FIGS. 2A and 2B where only one cameras hub is present).

Camera Carrier Bore-Based Medical System Configuration

Turning now to FIG. 10 and FIG. 11, the camera carrier 1 of the previous described embodiments is illustrated in a mounted position in a bore-based medical system 400. FIG. 10 illustrates one embodiment of the camera carrier, whereas FIG. 11 illustrates another exemplified embodiment of the camera carrier. It should be noted that the camera construction illustrated in FIG. 11 substantially corresponds to that of FIGS. 1A to 3 etc. Thus, in general, for FIGS. 10 and 11, the bore-based medical system 400 is configured to have mounted therein a camera carrier 1 according to any one of the previous described embodiments. The bore-based medical system 400 generally comprises a ring-gantry 407 comprising a radiotherapy beam, wherein said ring-gantry 407 surrounds a through-going bore 401 configured to receive a movable couch (not shown) configured to be moved into and out from the through-going bore 401. The through-going bore 401 is circumferentially defined by a bore wall whose inner surface 402 faces an inside of the bore. As illustrated in FIG. 10 and FIG. 11, the camera carrier 1 with its at least partly ring-shaped body 10 (as described in the previous embodiments) is configured to be mounted to the gantry housing 407 in connection with the bore wall. The mounting of the ring-shaped body 10 of the camera carrier 1 in the bore-based medical system is explained in more detail in relation to FIGS. 7 and 9 and reference is made thereto.

As further illustrated in FIG. 11, the bore-based medical system is configured with an iso-center and a setup focus point, wherein the setup focus point 24 is configured as a point of correct positioning of a patient in view of a target area of the patient to be treated, and where the iso-center focus point 23 is configured as a focus point at which an axis of rotation of the gantry, a collimator of the bore-based medical system and the treatment couch intersects. Please note that the gantry parts are substantially hidden within the bore structure of the bore-based medical system and is therefore not shown in further detail.

When the camera carrier 1 is mounted in the bore-based medical system 400 it is ensured that at least one of the one or more cameras is configured and oriented to comprise a field of view covering the iso-center 23 in a mounted stage of the camera carrier, and at least a second of the one or more cameras is configured and oriented to comprise a field of view covering the setup focus point 24 in a mounted stage of the camera carrier. Accordingly, as illustrated in FIG. 12 and previously explained in relation to the camera carrier, the cameras carrier 1 is configured to allow the front part cameras to cover a field of view intersecting at the setup focus point 24 of the bore-based medical system, and the back part cameras is configured to cover a field of view intersection at the iso-center focus point 23. This allows the camera carrier 1, as previous described, to monitor a patient during a setup-stage of the patient on the couch and during a treatment stage of the patient.

In FIG. 13 further details of an embodiment of the camera carrier according to FIGS. 2A and 2B is illustrated. As seen, the camera carrier 1 comprises the front part cameras 101a, 101b as in the previous described embodiments and also the back part cameras 201a, 201b. In addition, the camera carrier furthermore, in this embodiment is configured with the previous mentioned couch monitor camera 300 and at least one camera hub 129. As seen the camera hub 129 is positioned in another end of the camera carrier 1 than illustrated in FIGS. 2A and 2B and this is merely to illustrate other possible positions of the camera hub 129. Further the camera carrier 1 is in this embodiment further configured with LED's 30, which has the functions described herein to illuminate e.g. a calibration plate, retroreflective markers in the bore-based medical system and or to illuminate the patient to allow sufficient views of the patient lying on the couch. Thus, the LED's are pointing downwards to provide a "LED field of view" covering the couch of a bore-based medical system, when the camera carrier 1 is mounted therein. Further to these features, this embodiment also illustrates from a perspective top view of the camera carrier 1, the setup focus point 24 and the iso-center focus point 23 used by the camera carrier 1 when inserted into a bore-based medical system and as previously described.

In alternative embodiments, the camera carrier may be mounted as an integrated part of an inner side of the bore of the bore-based medical system. If referring to e.g. FIG. 10, the illustrated camera carrier is configured to be mounted on the inner surface 402 of the bore wall. In an alternative construction (not shown in more detail), the camera carrier may be arranged to be covered by the inner surface 402 and thus hidden within the internal construction of the gantry housing 407. In such embodiment, the bore wall would be configured with camera openings in the material of the bore wall so as to allow the cameras to look at the intended focus points of the bore-based medical system 400.

To ensure that the camera carrier is correctly positioned within the bore of the bore-based medical system, the camera carrier may in an embodiment be configured to have markers arranged thereon. In such embodiment, the markers are configured so that they enable an alignment with laser in the room of the bore-based medical system. The lasers in the room are standard features to ensure correct installation and calibration of the bore-based medical system in itself. These lasers can as described similarly be used to ensure that the camera carrier via aligning the markers with the lasers is positioned correctly within the bore of the bore-based medical system.

Furthermore, to ensure that the cameras are covering the right focus points of the bore-based medical system and that identical cameras can be used for the front part and back part cameras, the camera carrier is arranged within the through going bore 401 at a mid-point between the setup focus point and the iso-center.

Calibration of the Cameras of the Camera Carrier

To ensure that the cameras of the camera carrier are covering the correct field of views when inserted into the bore of the bore-based medical system a series of calibration steps may be used. It should be noted that the patient will be setup according to a pre-treatment plan, which provides information regarding the target area to be treated by radiotherapy and thus information regarding the positioning of the patient on the couch of a bore-based medical system in relation to an iso-center of the bore-based medical system. Thus, it is very important that the camera carrier is calibrated and mounted accurately in view of the iso-center of the bore-based medical system to allow motion tracking of the surface of the patient and thereby allow a health care professional to easily evaluate if a patient has moved out of position in view of the pre-planned target areas. Thus, such calibration methods steps will now be explained in more detail.

Figure 14:
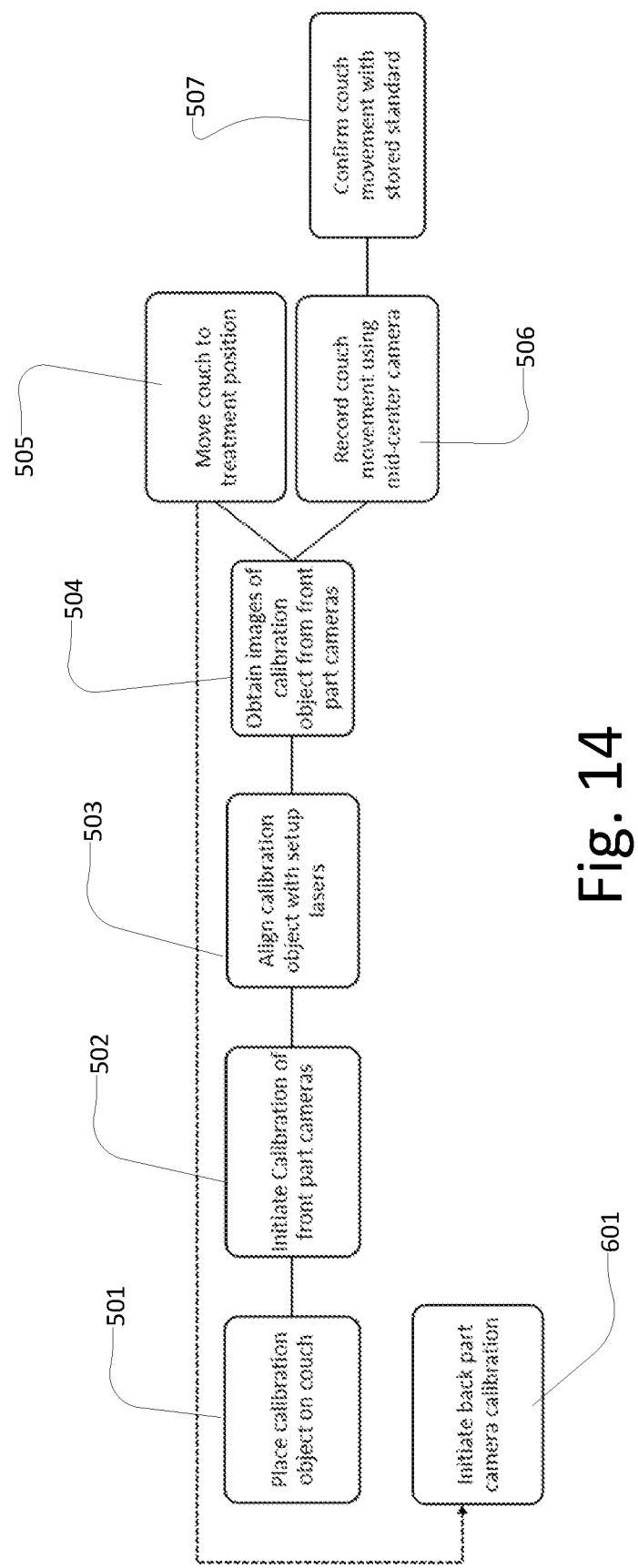
FIG. 14 illustrates a flow chart of the method utilized for calibration of the cameras.

Accordingly, in an embodiment illustrated in FIG. 14, the calibration of the cameras substantially follows the following steps. In a first step 501, after having mounted the camera carrier in the bore-based medical system, a calibration plate and/or phantom is positioned on a couch outside of the bore-based medical system. Subsequently in a second step 502, the front part camera calibration is initiated (i.e. a setup calibration). In this step 502, the calibration plate is initially 503 aligned with setup lasers in the bore-based medical treatment room. Subsequently in a step 504, the front part cameras is configured to obtain images of the calibration object. The following procedure of calibrating the front part cameras are substantially as described in published patent EP3218871B2, which is hereby incorporated by reference.

When the front part cameras have been calibrated, the couch is moved into the treatment position in a step 505 to allow calibration of the back part cameras to ensure correct iso-center field of view of the cameras and to ensure that the 3D reconstructed surface of the patient can be aligned with the iso-center configuration. This is needed to allow an accurate motion monitoring of the patient.

Before or alternatively at the same time as initiating the sub-sequent back-part camera calibration 601, the couch movement (distance, direction etc.) may be recorded and output to a processor of the system. This processor may be configured to compare the actual couch movement with preset couch movement data to allow a confirmation that the couch has moved as expected, see steps 506, 507. This is to ensure that the couch is moving as expected and thus that the calibration plate, phantom, or object is still positioned as expected in view of the iso-center of the bore-based medical system. Thus, in an embodiment, the couch monitoring camera may be actively monitoring the couch movement during the calibration steps.

After movement of the couch in step 505, the subsequent back part camera calibration 601 is initiated. The calibrations steps corresponding to the back part camera calibration 601 has been described in more detail in published patent EP3218871B2

In the calibration steps according to the disclosure, it should be noted that only one calibration object is used, wherein the calibration object is positioned at a position on the couch in the first front part camera calibration stage and stays at this position on the couch when the couch is moved into the bore and into the treatment position.

Accordingly, in an embodiment, the calibration object may comprise high friction feet to ensure that the calibration objects stay in the same location on the couch when the couch moves. If the calibration object moves away from the initial position, misalignment of the setup cameras (front par cameras) and treatment monitoring cameras (back part cameras) might occur, and thus avoiding by such high friction feet. Further, to evaluate if the calibration object itself has moved on the couch whilst moving the couch into the bore, a calibration object movement can be detected by referencing a new calibration with previous stored calibration data. In this way a quality check on the calibration object can be performed.

A further method of checking for inter-patient movement of the ring, is to record the plane of the unloaded couch before each patient is positioned there, and then compare the plane of the couch top. This should be completely consistent, if the plane of the couch top changes i.e. planes are at an angle to one another then the ring has been knocked and recalibration is required.

It should be noted that in an embodiment all of the cameras can be intrinsically calibrated prior to the calibration methods explained in relation to FIG. 14, where in this case the calibration object used in the bore-based system, will be used purely for extrinsic calibration. Alternatively, all cameras can be intrinsically and extrinsically calibrated by this process.

In an embodiment, the calibration object may optionally feature internal markers for co-calibration with the treatment system. That is, the cameras of the camera carrier may be configured to record images of an external surface of the calibration object, wherein the calibration object comprises blob features on the surface. In addition to this, the treatment system may be configured to record images of internal markers of the calibration object, wherein the internal markers are configured to light up on e.g. X-ray images taken by the treatment system. By taken into account the external surface images with the internal marker X-ray images it is possible to find a relationship between the two sets of images and determine the 3D transformations needed to map image data recorded from the camera carrier to a coordinate system of the treatment system. In this way it is ensured that the images provided by the camera carrier for motion monitoring is accurately aligned with the treatment system.

In an embodiment, the calibration object is a self-illuminated plate comprising 2 illumination wavelengths. This allows an illumination wavelength being configured to be recorded and seen by the video cameras but not by the visual eye of a human, whereas a second illumination wavelength is configured to be seen by the visual eye to allow a human person setting up the bore-based medical system for patient treatment etc, to visually align the calibration object to the bore-based medical system room laser.

The methods steps described herein may be performed by a computer-readable medium. In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

Further, the method may form part of a data processing system comprising a processor adapted to execute the computer program for causing the processor to perform at least some (such as a majority or all) of the steps of the method described herein.

It is intended that the structural features of the camera carrier and bore-based medical system, described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A bore-based radiotherapy medical system comprising:
a gantry having a housing configured to retain a radiotherapy beam source configured to emit a radiotherapy beam focused at an iso-center of the bore-based medical system; and
a camera carrier configured to be mounted on the gantry;
wherein the camera carrier includes at least one camera configured to be mounted in a direction toward a through-going bore and configured to cover a field of view including said iso-center focus point of the bore based medical system, wherein the at least one camera is configured to record images of a patient inside the through-going bore.

2. The bore-based radiotherapy medical system according to claim 1, wherein the at least one camera comprises two cameras.

3. The bore-based radiotherapy medical system according to claim 1, wherein the camera carrier is configured to be mounted inside an internal space of the gantry housing between the bore wall and an opposing wall of the gantry housing, or on a surface of the bore wall facing the through-going bore.

4. The bore-based radiotherapy medical system according to claim 3, further comprising a rotatable ring configured to retain a radiotherapy beam source configured to emit the radiotherapy beam, said rotatable ring being configured to rotate within the internal space of the gantry housing and at least partially around the through-going bore,
wherein at least one camera is configured to be mounted within said internal space, and
wherein the bore wall comprises an area transparent to wavelengths visible to the at least one camera, allowing the at least one camera to record images within the field of view including said iso-center focus point of the bore based medical system.

5. The bore-based radiotherapy medical system according to claim 2, wherein the camera carrier includes a ring-shaped or partially ring-shaped body, wherein the two cameras are configured to be mounted on the camera carrier at an equal distance from a focus point of the two cameras.

6. The bore-based radiotherapy medical system according to claim 1, wherein the carrier body comprises a camera viewing surface facing a focus point of the radiotherapy beam, and wherein the at least one camera is configured so that internal camera mirrors of at least one camera are configured to be angled in relation to the camera viewing surface.

7. The bore-based radiotherapy medical system according to claim 1, wherein the at least one camera comprises a projector configured to project a light onto a target configured to be arranged within a field of view of the at least one camera.

8. The bore-based radiotherapy medical system according to claim 1,
wherein the at least one camera comprises at least two internal mirrors including a first mirror and a second mirror,
wherein the first mirror is configured to be arranged at a first end surface of the at least one camera and the second mirror is configured to be arranged at a second end surface of the at least one camera,
wherein each of the first and second mirrors comprises a mirror center, and
wherein a mirror center axis is defined between the respective mirror centers of the first and second mirrors, the first and second mirrors being configured to reflect incoming light onto an image sensor of the at least one camera.

9. The bore-based radiotherapy medical system according to claim 8, wherein the first and second mirrors have respective mirror planes, each of the first and second mirrors being arranged so as to form a mirror angle between the corresponding mirror plane and a viewing surface of the at least one camera, the mirror angle of each of the first and second mirrors being equal to or greater than 45 degrees.

10. The bore-based radiotherapy medical system according to claim 9,
wherein the at least one camera comprise a substrate and first and second image sensors, the first image sensor being arranged on the substrate at a distance from the mirror center of the first mirror, the second image sensor being arranged at an opposite side of the substrate at a distance from the mirror center of the second mirror,
wherein the respective mirror planes of the first and second mirrors are configured such that the mirror angle $\alpha_1$ of the first mirror is equal to the mirror angle $\alpha_2$ of the second mirror, and
wherein the first image sensor comprises a first sensor axis and a second sensor axis perpendicular to the first sensor axis, and
wherein at least one of the first sensor axis and the second sensor axis is arranged normal to the plane of the viewing surface and parallel with a first mirror axis of the mirror plane of the first mirror.

11. The bore-based radiotherapy medical system according to claim 1, wherein the camera carrier further comprises at least one setup camera having a front viewing surface facing a front viewing area of the bore based medical system, wherein the at least one camera is configured with a field of view covering at least a part of a movable couch when the couch is positioned outside of the through-going bore, the couch being configured to be moved into and out from the through-going bore.

12. The bore-based radiotherapy medical system according to claim 11, wherein the at least one camera comprises two cameras and the at least one set up camera comprises two setup cameras.

13. The bore-based radiotherapy medical system according to claim 12, wherein each of the two setup cameras is configured to be mounted in relation to the bore based system substantially back to back with a corresponding one of the two cameras so as to form a first back-to-back and a second back-to-back camera configuration.

14. The bore-based radiotherapy medical system according to claim 13,
wherein the camera carrier comprises a couch monitoring camera,
wherein the couch monitoring camera is configured to be mounted in relation to said bore based medical system so as to be substantially mid-centered in relation to the first back-to-back and second back-to-back camera configuration, and
wherein the couch monitoring camera is configured with a lens orientation having a field of view covering at least a part of the couch in a mounted state of the couch monitoring camera.

15. The bore-based radiotherapy medical system according to claim 2, where in the camera carrier incudes a partly ring-shaped body comprising a first arch having a front body part and a back body part,
wherein the front and back body parts are configured to be connected so as to form a width of the partly ring-shaped body, and
wherein the two cameras are configured to be mounted on the camera carrier at the partly ring-shaped body at an equal distance from a focus point of the two cameras.

16. The bore-based radiotherapy medical system according to claim 15, wherein the camera carrier is configured to be mounted inside an internal space of the gantry housing between the bore wall and an opposing wall of the gantry housing, or on a surface of the bore wall facing the through-going bore.

17. The bore-based radiotherapy medical system according to claim 16, wherein the first arch is configured to be mounted within the internal space of the gantry housing.

18. The bore-based radiotherapy medical system according to claim 16,
wherein one end of the first arch is configured to be connected to a left arch, and the other end of the first arch is configured to be connected to a right arch,
wherein each of the left and right arches is configured to be connected via a substantially flexible joint to a hinge so as to form a full-ring shaped camera carrier configured to be mounted inside the internal space of the gantry housing or on the surface of the bore wall.

19. The bore-based radiotherapy medical system according to claim 18,
wherein the left and right arches are configured to be connected through an adjustable expansion element,
wherein the expansion element is configured to be adjusted to a first expansion stage forcing the left and right arch away from each other, and to a second stage relieving the first expansion stage.

* * * * *